United States Patent
Biris et al.

(10) Patent No.: US 12,099,059 B2
(45) Date of Patent: *Sep. 24, 2024

(54) NANOCOMPOSITES, METHODS OF MAKING SAME, AND APPLICATIONS OF SAME FOR MULTICOLOR SURFACE ENHANCED RAMAN SPECTROSCOPY (SERS) DETECTIONS

(71) Applicant: BOARD OF TRUSTEES OF THE UNIVERSITY OF ARKANSAS, Little Rock, AR (US)

(72) Inventors: Alexandru S. Biris, Little Rock, AR (US); Zeid Nima, Little Rock, AR (US); Yang Xu, Little Rock, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 804 days.

This patent is subject to a terminal disclaimer.

(21) Appl. No.: 17/037,830

(22) Filed: Sep. 30, 2020

(65) Prior Publication Data

US 2021/0041431 A1 Feb. 11, 2021

Related U.S. Application Data

(62) Division of application No. 15/697,055, filed on Sep. 6, 2017, now Pat. No. 10,830,767, which is a division
(Continued)

(51) Int. Cl.
*G01N 33/543* (2006.01)
*G01N 33/553* (2006.01)

(52) U.S. Cl.
CPC . *G01N 33/54346* (2013.01); *G01N 33/54353* (2013.01); *G01N 33/553* (2013.01)

(58) Field of Classification Search
None
See application file for complete search history.

(56) References Cited

U.S. PATENT DOCUMENTS 9,810,687 B2 * 11/2017 Biris ............... G01N 21/658
11,119,099 B2 * 9/2021 Biris ............... G01N 33/54346
(Continued)

FOREIGN PATENT DOCUMENTS

CN 102398043 A * 4/2012

OTHER PUBLICATIONS

Machine translation of CN 102398043 A, Apr. 2012. (Year: 2012).*
(Continued)

*Primary Examiner* — Carlos A Azpuru
*Assistant Examiner* — Casey S Hagopian
(74) *Attorney, Agent, or Firm* — Locke Lord LLP; Tim Tingkang Xia, Esq.

(57) ABSTRACT

A method of making at least one nanocomposite for surface enhanced Raman spectroscopy (SERS) detection of a target of interest includes forming at least one gold nanorod; coating a silver layer on an outer surface of the gold nanorod; assembling a Raman reporter molecule layer on the coated silver layer, wherein the Raman reporter molecule layer comprises Raman reporter molecules that are detectable by the SERS; coating a thiolated polyethylene glycol (PEG) layer on the assembled Raman reporter molecule layer; and conjugating the coated thiolated PEG layer with molecules of an antibody to make the at least one nanocomposite.

9 Claims, 10 Drawing Sheets

Related U.S. Application Data of application No. 14/513,744, filed on Oct. 14, 2014, now Pat. No. 9,784,737.

(60) Provisional application No. 61/891,006, filed on Oct. 15, 2013.

(56) References Cited

U.S. PATENT DOCUMENTS

| | | | |
|---|---|---|---|
| 2011/0165077 A1* | 7/2011 | Qian | A61K 49/0023 424/9.1 |
| 2012/0014878 A1* | 1/2012 | Culha | C07H 21/00 424/9.1 |

OTHER PUBLICATIONS

Huang et al. ("Surface-enhance Raman spectroscopic study of p-aminothiophenol" Phys. Chem. Chem. Phys., 2012, 14, 8485-8497 (Year: 2012).*

* cited by examiner

NANOCOMPOSITES, METHODS OF MAKING SAME, AND APPLICATIONS OF SAME FOR MULTICOLOR SURFACE ENHANCED RAMAN SPECTROSCOPY (SERS) DETECTIONS

CROSS-REFERENCE TO RELATED APPLICATIONS

This application is a divisional application of and claims the benefit of U.S. patent application Ser. No. 15/697,055, filed Sep. 6, 2017, now allowed, which itself is a divisional application of and claims the benefit of U.S. patent application Ser. No. 14/513,744, filed Oct. 14, 2014, now U.S. Pat. No. 9,784,737, which itself claims priority to and the benefit of U.S. provisional patent application Ser. No. 61/891,006, filed Oct. 15, 2013, which are incorporated herein in their entireties by reference.

STATEMENT AS TO RIGHTS UNDER FEDERALLY-SPONSORED RESEARCH

This invention was made with government support under grant number W81XWH-10-2-0130 awarded by the Department of Defense. The government has certain rights in the invention.

Some references, which may include patents, patent applications, and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [3] represents the third reference cited in the reference list, namely, Nima, Z. A. et al. Single-walled carbon nanotubes as specific targeting and Raman spectroscopic agents for detection and discrimination of single human breast cancer cells. *Journal of Biomedical Optics* 18, 055003-055003 (2013).

FIELD OF THE INVENTION

The invention relates generally to detections of cancer cells or pathogens, and more particularly to nanocomposites, methods of making the same, and applications of the same for multicolor surface enhanced Raman spectroscopy (SERS) detections and imaging of cancer cells or pathogens.

BACKGROUND OF THE INVENTION

The background description provided herein is for the purpose of generally presenting the context of the present invention. Work of the presently named inventors, to the extent it is described in this background section, as well as aspects of the description that may not otherwise qualify as prior art at the time of filing, are neither expressly nor impliedly admitted as prior art against the present invention.

Targeting, imaging and treatment of cancer cells using biocompatible nanomaerials is one ultimate goal for a versatile number of studies in different fields of science, engineering, and medicine [1-9]. Nanomaterials are widely investigated and tested by researchers from different fields due to their unique features not observed at the macroscale of the same material [1, 2]. However, there are still challenges in the field to discover nanoagents that provide sensitive and accurate detection of cancer cells.

Therefore, a heretofore unaddressed need exists in the art to address the aforementioned deficiencies and inadequacies.

SUMMARY OF THE INVENTION

In one aspect, the invention is directed to a nanoagent for surface enhanced Raman spectroscopy (SERS) detection of a target of interest. In certain embodiments, the nanoagent includes at least one nanocomposite.

In one embodiment, the nanocomposite includes at least one gold nanorod, a silver layer coated on an outer surface of the gold nanorod and having silver nanoparticles, a Raman reporter molecule layer coated on the silver layer, a pegylated layer coated on the Raman reporter molecule layer and having at least one of thiolated polyethylene glycol (HS-PEG), thiolated polyethylene glycol acid (HS-PEG-COOH) and HS-PEG-NHx, and an antibody layer conjugated to the pegylated layer and having molecules of an antibody.

In one embodiment, the gold nanorod has an aspect ratio (AR) in the range of about 1-9. In one embodiment, the gold nanorod has the AR in a range of about 2-5. In one embodiment, the gold nanorod has the AR in a range of about 2.77-3.23.

In one embodiment, the gold nanorod has a length in the range of about 10-100 nm and has a diameter in the range of about 1-40 nm, respectively. In one embodiment, the gold nanorod has the length in the range of about 35.20-36.80 nm and has the diameter in the range of about 11.59-12.41 nm, respectively.

In one embodiment, the silver layer has a thickness in a range of about 0.5-5 nm. In one embodiment, the silver layer has the thickness of about 1-2 nm. In one embodiment, the silver layer has the thickness of about 1.7 nm.

In one embodiment, the Raman reporter molecule layer includes 4-mercaptobenzoic acid (4MBA), p-aminothiophenol (PATP), p-nitrothiophenol (PNTP), 4-(methylsulfanyl) thiophenol (4MSTP), or other molecules with unique Raman spectra and intense Raman peak intensities.

In one embodiment, the HS-PEG has a molecular weight in a range of about 1.5-15 kilo Dalton (kD) and the HS-PEG-COOH has a molecular weight in a range of about 1-10 kD. In one embodiment, the HS-PEG has the molecular weight of about 5 kD and the HS-PEG-COOH has the molecular weight of about 3 kD.

In one embodiment, the molecules of the antibody are conjugated to the corresponding pegylated layer through the carboxylic group of the HS-PEG-COOH or the amine group of HS-PEG-NHx.

In one embodiment, the antibody anti-epithelial cell adhesion molecule antibody (anti-EpCAM), anti-CD44 antibody, anti-insulin-like growth factor 1 receptor antibody (anti-IGF-1), anti-Keratin 18 antibody, or one or more antibodies specific to the target of interest.

In one embodiment, the at least one nanocomposite includes a first nanocomposite, a second nanocomposite, a third nanocomposite, and a fourth nanocomposite. The Raman reporter molecule layer of the first nanocomposite includes 4-mercaptobenzoic acid (4MBA), and the antibody of the first nanocomposite is anti-epithelial cell adhesion molecule antibody (anti-EpCAM). The Raman reporter molecule layer of the second nanocomposite includes p-aminothiophenol (PATP), and the antibody of the second nanocomposite is anti-CD44 antibody. The Raman reporter molecule layer of the third nanocomposite is p-nitrothiophenol (PNTP), and the antibody of the third nanocomposite is anti-insulin-like growth factor 1 receptor antibody (anti-IGF-1). The Raman reporter molecule layer of the fourth nanocomposite comprises 4-(methylsulfanyl) thiophenol (4MSTP), and the antibody of the fourth nanocomposite is anti-Keratin 18 antibody.

In one embodiment, SERS signal corresponding to each nanocomposite is represented by a predetermined color.

In one embodiment, the target of interest includes at least one tumor cell or at least one pathogen.

In certain embodiments, the nanocomposite further includes one or more molecules of interest attached to the pegylated layer or the antibody layer.

In one embodiment, the molecule of interest is a growth factor that induces certain biological functions, including the growth, proliferation of differentiation of cells or organisms.

In one embodiment, the molecule of interest is a protein, a drug, or a biological system that induces certain biological functions, the death of cells, tissues, or organisms. The one or more drugs may be anticancer drugs, antibiotics, or antiviral drugs.

In one embodiment, the nanocomposite further includes one or more fluorescent agents. The one or more fluorescent agents can be quantum dots or fluorescent dyes. The one or more fluorescent agents may be mixed with the Raman report molecules and located at the Raman reporter layer, may be attached to or located at the antibody layer, or may be formed of a separate layer.

In another aspect, the present invention is directed to a nanocomposite. In one embodiment, the nanocomposite includes a core, a shell surrounding the core, a reporter layer assembled on the shell, comprising a reporter molecule, and a targeting layer conjugated to the reporter layer, comprising targeting molecules.

In one embodiment, the core includes at least one gold nanorod, and the shell is a silver layer comprising silver nanoparticles.

In one embodiment, the reporter molecule layer is detectable by at least one of surface enhanced Raman spectroscopy (SERS), magnetic resonance imaging (MRI), x-ray radiography, computed tomography (CT), positron emission tomography-computed tomography (PET-CT), and infrared spectroscopy (IR).

In one embodiment, the reporter molecule comprises 4MBA, PATP, PNTP, 4MSTP, or other molecules with unique Raman spectra and intense Raman peak intensities.

In one embodiment, the nanocomposite further includes a pegylated layer disposed between the reporter layer and the targeting layer, and the pegylated layer has at least one of HS-PEG, HS-PEG-COOH and HS-PEG-NHx.

In one embodiment, the targeting molecules are molecules of anti-EpCAM antibody, anti-CD44 antibody, anti-IGF-1 antibody, or anti-Keratin 18 antibody, or one or more antibodies specific to the target of interest.

In certain embodiments, the nanocomposite further includes one or more molecules of interest attached to the pegylated layer or the antibody layer. In one embodiment, the molecule of interest is a growth factor that induces certain biological functions, including the growth, proliferation of differentiation of cells or organisms.

In one embodiment, the molecule of interest is a protein, a drug, or a biological system that induces certain biological functions, the death of cells, tissues, or organisms. The one or more drugs may be anticancer drugs, antibiotics, or antiviral drugs.

In one embodiment, the nanocomposite further includes one or more fluorescent agents. The one or more fluorescent agents can be quantum dots or fluorescent dyes. The one or more fluorescent agents may be mixed with the other report molecules and located at the reporter layer, may be attached to or located at the targeting layer, or may be formed of a separate layer.

In one embodiment, the present invention is directed to a nanoagent including at least one nanocomposite as described above, for detecting at least one tumor cell or at least one pathogen.

In a further aspect, the present invention is directed to a system for detecting a target of interest. In certain embodiments, the system includes a nanoagent having at least one nanocomposite, a surface enhanced Raman spectrometer, and a processing unit. The nanocomposite includes at least one gold nanorod, a silver layer coated on an outer surface of the gold nanorod and having silver nanoparticles, a Raman reporter molecule layer assembled on the silver layer, a pegylated layer coated on the Raman reporter molecule layer and having at least one of HS-PEG, HS-PEG-COOH and HS-PEG-NHx, and an antibody layer conjugated to the pegylated layer and having molecules of an antibody. The surface enhanced Raman spectrometer is configured to provide an incident radiation signal to the target of interest, and to collect SERS signals generated by the Raman reporter molecule layer in response to the incident radiation signal. The processing unit is configured for processing the SERS signals collected by the surface enhanced Raman spectrometer, so as to determine whether the target of interest has at least one tumor cell or at least one pathogen.

In one embodiment, the at least one nanocomposite includes a first nanocomposite, a second nanocomposite, a third nanocomposite, and a fourth nanocomposite. The Raman reporter molecule layer of the first nanocomposite includes 4MBA, and the antibody of the first nanocomposite is anti-EpCAM antibody. The Raman reporter molecule layer of the second nanocomposite includes PATP, and the antibody of the second nanocomposite is anti-CD44 antibody. The Raman reporter molecule layer of the third nanocomposite includes PNTP, and the antibody of the third nanocomposite is anti-IGF-1 antibody. The Raman reporter molecule layer of the fourth nanocomposite includes 4MSTP, and the antibody of the fourth nanocomposite is anti-Keratin 18 antibody.

In one embodiment, the SERS signals corresponding to the first, the second, the third, and the fourth nanocomposites are characterized with different colors respectively.

In one embodiment, the nanorod has an AR in a range of about 1-9. In one embodiment, the nanorod has the AR in the range of about 2-5. In one embodiment, the nanorod has the AR in the range of about 2.77-3.23.

In one embodiment, the nanorod has a length in a range of about 10-100 nm and has a diameter in a range of about 1-40 nm, respectively. In one embodiment, the nanorod has the length in a range of about 35.20-36.80 nm and has the diameter in a range of about 11.59-12.41 nm, respectively.

In one embodiment, the silver layer has a thickness in a range of about 0.5-5 nm. In one embodiment, the silver layers have a thickness of about 1-2 nm. In one embodiment, the silver layers have a thickness of about 1.7 nm.

In one embodiment, the HS-PEG has a molecular weight in a range of about 1.5-15 kilo Dalton (kD) and the HS-PEG-COOH has a molecular weight in a range of about 1-10 kD.

In one embodiment, the HS-PEG has the molecular weight of about 5 kD and the HS-PEG-COOH has the molecular weight of about 3 kD.

In one embodiment, the at least one target includes at least one tumor cell or at least one pathogen.

In certain embodiments, the nanocomposite further includes one or more molecules of interest attached to the pegylated layer or the antibody layer.

In one embodiment, the molecule of interest is a growth factor that induces certain biological functions, including the growth, proliferation of differentiation of cells or organisms.

In one embodiment, the molecule of interest is a protein, a drug, or a biological system that induces certain biological functions, the death of cells, tissues, or organisms. The one or more drugs may be anticancer drugs, antibiotics, or antiviral drugs.

In one embodiment, the nanocomposite further includes one or more fluorescent agents. The one or more fluorescent agents may be quantum dots or fluorescent dyes. The one or more fluorescent agents may be mixed with the Raman report molecules and located at the Raman reporter layer, may be attached to or located at the antibody layer, or may be formed of a separate layer.

In yet another aspect, the present invention is directed to a method of making at least one nanocomposite for SERS detection of a target of interest. In certain embodiments, the method includes:

forming at least one gold nanorod;

coating a silver layer on an outer surface of the gold nanorod;

assembling a Raman reporter molecule layer on the coated silver layer, wherein the Raman reporter molecule layer includes Raman reporter molecules detectable by the SERS;

coating a thiolated polyethylene glycol (PEG) layer on the assembled Raman reporter molecule layer; and conjugating the coated thiolated PEG layer with molecules of an antibody to make the at least one nanocomposite.

In one embodiment, the step of forming the at least one gold nanorod includes:

mixing a first hexadecyltrimethylammoniumbromide (CTAB) solution with a silver nitrate solution to form a first mixture;

adding a first $HAuCl_4$ to the first mixture to form a second mixture;

adding a first ascorbic acid to the second mixture to form a third mixture;

adding a seed solution to the third mixture to form a fourth mixture; and centrifuging the fourth mixture to form a first precipitate, wherein the first precipitate comprises the gold nanorod.

In one embodiment, the seed solution is prepared by:

mixing a second CTAB solution with a second $HAuCl_4$ to form a fifth mixture; and adding $NaBH_4$ to the fifth mixture and stirring to form the seed solution.

In one embodiment, the step of coating the silver layer includes:

dispersing the gold nanorod in a third CTAB solution by sonication to form a sixth mixture;

adding a polyvinylpyrrolidone (PVP) solution and $AgNO_3$ to the sixth mixture and gently mixing to form a seventh mixture;

adding a second ascobic acid to the seventh mixture to form an eighth mixture;

adding NaOH solution to the eighth mixture to form a ninth mixture, such that the pH of the ninth mixture is elevated to about pH9, and a silver ion reduction reaction is initiated; and centrifuging the ninth mixture to form a second precipitate, wherein the second precipitate comprises gold nanorod coated with the silver layer.

In one embodiment, the step of assembling the Raman reporter molecule layer includes:

dispersing the gold nanorod coated with the silver layer in distilled water to form a tenth mixture;

dissolving the Raman reporter molecule selected from the group consisting of 4-MBA, PATP, PNTP, and 4-MSTP, in ethanol to form a reporter solution;

adding the reporter solution to the tenth mixture and stirring for to form an eleventh mixture; and centrifuging the eleventh mixture to form a third precipitate, wherein the third precipitate comprises the gold nanorod coated with the silver layer, and assembled with the Raman reporter molecule layer.

In one embodiment, the step of coating the thiolated PEG layer includes: dispersing the gold nanorod with the coated silver layer and the assembled Raman report molecule layer in HS-PEG-COOH solution and vigorously stirring to form a twelfth mixture, wherein the HS-PEG-COOH solution comprises about 2 mg/ml HS-PEG and about 2 mM NaCl;

adding HS-PEG to the twelfth mixture and keep at about 5° C. overnight to form a thirteenth mixture; and centrifuging the thirteenth mixture to form a fourth precipitate, wherein the fourth precipitate comprises the gold nanorod coated with the silver layer, assembled with the Raman reporter molecule layer, and coated with the thiolated PEG layer.

In one embodiment, the step of conjugating the pegylated-Raman-silver coated gold nanorod with an antibody includes:

suspending the gold nanorod coated with the silver layer, assembled with the Raman reporter molecule layer, and coated with the thiolated PEG layer in PBS buffer by sonicating to form a suspending mixture;

adding N-hydroxysuccinimide (NETS) and 1N-ethyl-N'-(3-dimethylaminopropyl) carbodiimide hydrochloride (EDC) to the suspending mixture and stirring to form a fourteenth mixture;

washing the fourteenth mixture by centrifuging twice using PBS buffer to obtain a fourth precipitate;

dispending the fourth precipitate in PBS buffer to form a fifteen mixture;

adding the molecules of the antibody to the fifteenth mixture and mixing thoroughly to form a sixteen mixture, wherein the antibody includes anti-EpCAM, anti-CD44, anti-IGF-1 Receptor β, anti-Keratin 18, and one or more antibodies specific to the target of interest; and stirring the sixteenth mixture at room temperature to form the nanocomposite.

In one embodiment, SERS signal corresponding to each nanocomposite is characterized with a predetermined color.

In one embodiment, a method of making a nanoagent is provided, and the nanoagent includes one or more nanocomposite produced by the method described above.

In certain embodiments, the method further includes attaching one or more molecules of interest to the pegylated layer or the antibody layer.

In one embodiment, the molecule of interest is a growth factor that induces certain biological functions, including the growth, proliferation of differentiation of cells or organisms.

In one embodiment, the molecule of interest is a protein, a drug, or a biological system that induces certain biological functions, the death of cells, tissues, or organisms. The one or more drugs may be anticancer drugs, antibiotics, or antiviral drugs.

In one embodiment, the method further includes attaching one or more fluorescent agents to the nanocomposite. The one or more fluorescent agents may be quantum dots or fluorescent dyes. The one or more fluorescent agents may be mixed with the Raman report molecules before the assemble step, so that the assembled Raman reporter molecule layer contains the one or more fluorescent agents. In other embodiments, the one or more fluorescent agents may also be attached to or located at the antibody layer, or may be formed of a separate layer.

Further areas of applicability of the invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The following figures form part of the present specification and are included to further demonstrate certain aspects of the invention. The invention may be better understood by reference to one or more of these figures in combination with the detailed description of specific embodiments presented herein. The drawings described below are for illustration purposes only. The drawings are not intended to limit the scope of the present teachings in any way.

DETAILED DESCRIPTION OF THE INVENTION

Figure 1:
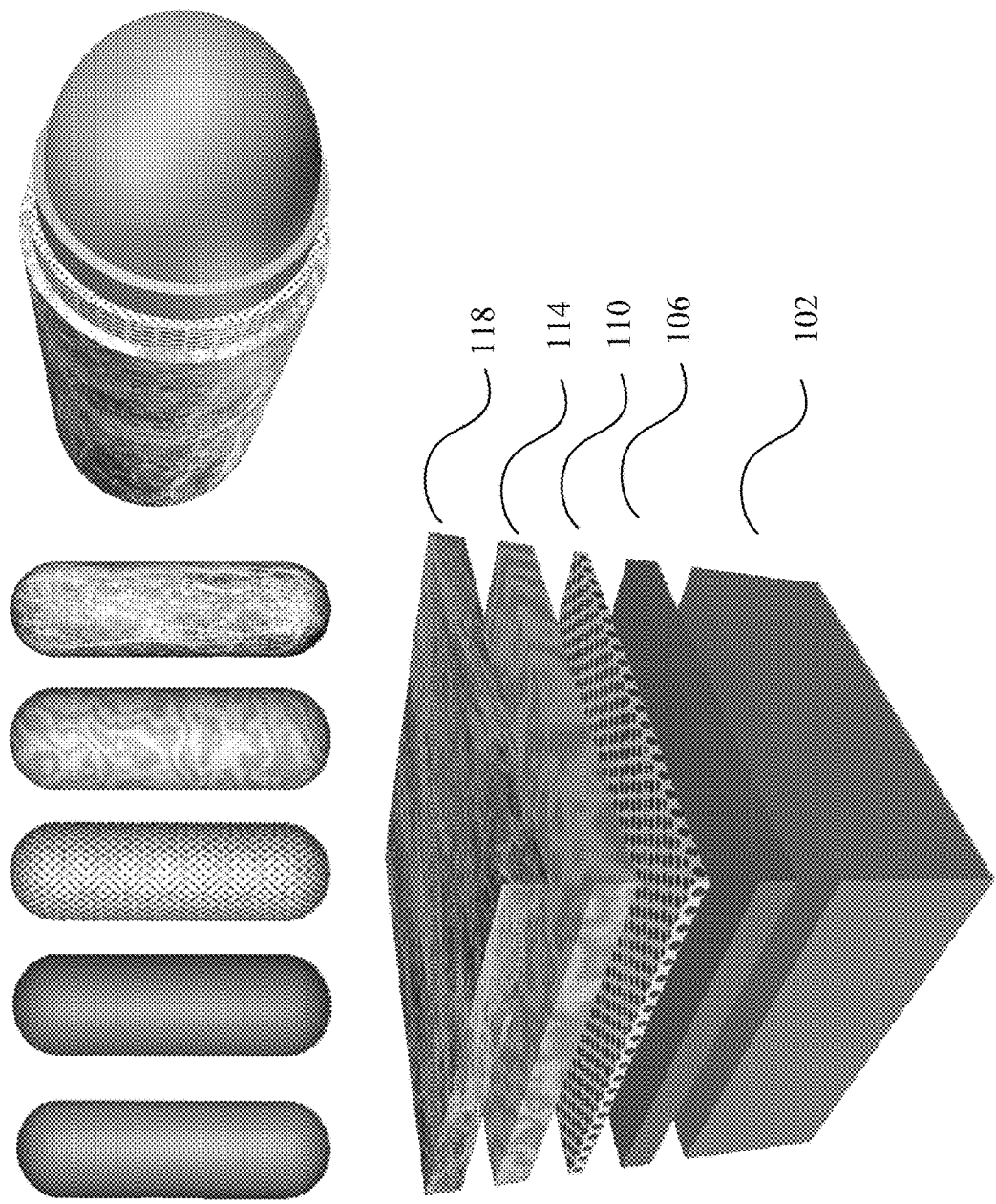
FIG. 1 schematically shows a nanocomposite of a nanoagent according to one embodiment of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

As used herein, "around", "about", "substantially" or "approximately" shall generally mean within 20 percent, preferably within 10 percent, and more preferably within 5 percent of a given value or range. Numerical quantities given herein are approximate, meaning that the terms "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the term "MCF-7" refers to a breast cancer cell line isolated in 1970 from a 69-year-old Caucasian woman. MCF-7 is the acronym of Michigan Cancer Foundation-7, referring to the institute in Detroit where the cell line was established in 1973 by Herbert Soule and co-workers. The Michigan Cancer Foundation is now known as the Barbara Ann Karmanos Cancer Institute. Prior to MCF-7, it was not possible for cancer researchers to obtain a mammary cell line that was capable of living longer than a few months. The patient, whose name, Frances Mallon, is unknown to the vast majority of cancer researchers, died in 1970. Her cells were the source of much of current knowledge about breast cancer. At the time of sampling, she was a nun in the convent of Immaculate Heart of Mary in Monroe, Michigan under the name of Sister Catherine Frances. MCF-7 and two other breast cancer cell lines, named T-47D and MDA-MB-231, account for more than two-thirds of all abstracts reporting studies on mentioned breast cancer cell lines, as concluded from a Medline-based survey.

As used herein, the term "BJ-1 cell line" refers to a normal skin fibroblast cell line, which is available from American Type Culture Collection (ATCC) with ATCC number CRL-2522.

As used herein, the term "circulating tumor cells" or "CTCs" refers to cells that have shed into the vasculature from a primary tumor and circulate in the bloodstream. CTCs thus constitute seeds for subsequent growth of additional tumors (metastasis) in vital distant organs, triggering a mechanism that is responsible for the vast majority of cancer-related deaths.

As used herein, the term "DMEM" refers to Dulbecco's Modified Eagle Medium, and EMEM is the abbreviation of Eagle's Minimum Essential Medium.

As used herein, the term "ICC" refers to the abbreviation of immunocytochemistry staining.

As used herein, the term "4MBA" refers to 4-mercaptobaezoic acid, PNTP is the abbreviation of p-nitrobenzoic acid, PATP is the abbreviation of p-aminobenzoic acid, 4MSTP is the abbreviation of 4-methylsulfanyl thiophenol, and 4APDS is the abbreviation of 4-aminophenyldisulfide.

As used herein, the term "HS-PEG-COOH and HS-PEG" refer to thiolated polyethylene glycol with or without acid terminal, respectively.

As used herein, the term "phosphate buffered saline" or "PBS" refers to a buffer solution commonly used in biological research. It is a water-based salt solution containing sodium phosphate, sodium chloride and, in some formulations, potassium chloride and potassium phosphate. The osmolarity and ion concentrations of the solutions match those of the human body (isotonic).

As used herein, the term "bovine serum albumin" or "BSA" or "Fraction V" refers to a serum albumin protein derived from cows. It is often used as a protein concentration standard in lab experiments.

As used herein, the term "fetal bovine serum" or "FBS" or "fetal calf serum" refers to the blood fraction remaining after the natural coagulation of blood, followed by centrifugation to remove any remaining red blood cells. Fetal bovine serum comes from the blood drawn from a bovine fetus via a closed system of collection at the slaughterhouse. Fetal bovine serum is the most widely used serum-supplement for the in vitro cell culture of eukaryotic cells. This is due to it having a very low level of antibodies and containing more growth factors, allowing for versatility in many different cell culture applications.

OVERVIEW OF THE INVENTION

The conjugation of the nanomaterials with targeting molecules such as antibodies, folates, aptamer or immune protein could provide specific delivery of the nanomaterials to various cancer cell lines, within minutes [3-8]. Recently, quantum dot nanomaterials and iron oxide nanoparticles have been used widely as imaging and diagnostic nanoagents for cancer cells [16-18]. Among these new and enhanced imaging and diagnostic assays, surface-enhanced Raman spectroscopy (SERS) has been studied and proposed for early imaging and detection [19-22] of tumor cells.

In one aspect, the present invention is directed to a biocompatible nanoagent for detecting a target of interest by SERS. In certain embodiments, the target may include at least one tumor cell or at least one pathogen. The tumor cell can be a benign tumor cell or a malignant tumor cell. The malignant tumor cell, or a cancer cell, can be located locally or a circulating tumor cell (CTC). The pathogen can be a virus, bacterium, prion, fungus or protozoan that causes disease in its host. In certain embodiments, the nanoagent includes at least one nanocomposite, such as four different types of nanocomposites.

In one embodiment, the nanocomposite includes at least one gold nanorod, a silver layer coated on an outer surface of the gold nanorod and having silver nanoparticles, a Raman reporter molecule layer coated on the silver layer and having Raman reporter molecules, a pegylated layer coated on the Raman reporter molecule layer and having at least one of thiolated polyethylene glycol (HS-PEG), thiolated polyethylene glycol acid (HS-PEG-COOH) and HS-PEG-NHx, and an antibody layer conjugated to the pegylated layer and having molecules of an antibody. In one embodiment, the AR of the gold nanorod is in a range of 2-5. In one embodiment, the AR of the gold nanorod is in a range of 2.77-3.23 or is about 3±0.23, and the length and the diameter of the gold nanorod is in a range of about 35.20-36.80 and about 11.59-12.41 respectively, or about 36±0.80 nm and about 12±0.41 nm, respectively, and the thickness of the silver layer is about 1-2 nm, or about 1.7 nm.

In one embodiment, the at least one nanocomposite includes a first nanocomposite, a second nanocomposite, a third nanocomposite, and a fourth nanocomposite. The Raman reporter molecule layer of the first nanocomposite includes 4-mercaptobenzoic acid (4MBA), and the antibody of the first nanocomposite is anti-epithelial cell adhesion molecule antibody (anti-EpCAM). The Raman reporter molecule layer of the second nanocomposite includes p-aminothiophenol (PATP), and the antibody of the second nanocomposite is anti-CD44 antibody. The Raman reporter molecule layer of the third nanocomposite includes p-nitrothiophenol (PNTP), and the antibody of the third nanocomposite is anti-insulin-like growth factor 1 receptor antibody (anti-IGF-1). The Raman reporter molecule layer of the fourth nanocomposite includes 4-(methylsulfanyl) thiophenol (4MSTP), and the antibody of the fourth nanocomposite is anti-Keratin 18 antibody.

In one embodiment, SERS signal corresponding to each nanocomposite is represented by a predetermined color, such that SERS signals of the nanoagent having multiple nanocomposites are represented by multiple colors.

In another aspect, the present invention is directed to a system for detecting a target of interest. In certain embodiments, the target of interest includes at least one tumor cell or at least one pathogen. In certain embodiments, the system includes a nanoagent as described above that has multiple nanocomposites, a surface enhanced Raman spectrometer configured to provide an incident radiation signal to the target of interest, and to collect surface enhanced Raman spectroscopy (SERS) signals generated by the Raman reporter molecule layer in response to the incident radiation signal, and a processing unit for processing the SERS signals collected by the surface enhanced Raman spectrometer to determine whether the target of interest have at least one tumor cell or at least one pathogen.

In a further aspect, the present invention is directed to a method of making a nanocomposite or a nanoagent having one or more nanocomposites, where the nanocomposite/nanocomposites have the structures as described above, and the nanocomposite/nanoagent can be used for surface enhanced Raman spectroscopy (SERS) detection of a target of interest, such as at least one tumor cell or at least one pathogen.

In one embodiment, the method includes: forming a gold nanorod, coating a silver layer on an outer surface of the gold nanorod; assembling a Raman reporter molecule layer on the coated silver layer, wherein the Raman reporter molecule layer includes Raman reporter molecules that are detectable by the SERS; coating a thiolated polyethylene glycol (PEG) layer on the assembled Raman reporter molecule layer; and conjugating the coated thiolated PEG layer with molecules of an antibody to make the nanocomposite.

Anti-EpCam antibody, anti-CD44 antibody, anti-keratin 18 antibody, anti-IGF-I antibody, and one or more antibodies specific to the target of interest are used in the present invention.

Since the epithelial cell adhesion molecule (EpCam) antigen is highly expressed in normal epithelial cells and the MCF-7 cells originating from these cells, the cells express a considerable amount of EpCam antigen on their surface. Because the EpCam antigen is greatly over-expressed in many types of cancers, including colon, hepatic, pancreatic, prostate, and breast cancer [32], Anti-EpCam has been used extensively in breast cancer detection.

CD44 is a cell-cell and cell-matrix adhesion molecule known to be highly expressed in many types of cancers and widely used in the diagnosis and prognosis of breast cancer [33, 34]. CD44 is important in tumor development and progression, and anti-CD44 provides multiple prospects for advanced cancer treatments by targeting therapeutics to the CD44 receptor of the metastasizing tumors, interfering with the CD44 signaling pathway.

Keratin 18 is known to be highly expressed in normal mammary epithelial cells, and MCF-7 cells are adenocarcinoma derived from simple breast epithelium. In one embodiment, anti-keratin 18 antibodies have been used in diagnostic histopathology of breast cancer. In addition, it has been shown that the down-regulation of membrane keratin 18 plays a key role in the prognosis of the breast cancer patient [35].

Insulin-like growth factor 1 (IGF-I) is expressed in 90% of breast cancer specimens. Therefore, the anti-IGF-I antibody is used as an molecule to target breast cancer cells [36, 37].

These and other aspects of the invention are more specifically described below.

Implementations and Examples of the Invention

Without intend to limit the scope of the invention, further exemplary procedures and preliminary experimental results of the same according to the embodiments of the invention are given below.

In one aspect, the present invention is directed to a biocompatible nanoagent for detecting a target of interest, such as at least one cancer cell or at least one pathogen, by SERS. In certain embodiments, the biocompatible nanoagent includes one or more nanocomposites.

FIG. 1 schematically shows a nanocomposite of a nanoagent according to one embodiment of the invention. Referring to FIG. 1, each of the nanocomposite 100 includes a core 102, a shell 106 wrapped around the core 102, a reporter layer 110 assembled on the shell 106, a binding layer 114 coated on the reporter layer 110, and a targeting layer 118 conjugated to the binding layer 114.

In certain embodiments, the core 102 is a gold nanorod (AuNR). The aspect ratio (AR) is defined as the ratio of the length of the AuNR to the diameter of the AuNR. In one embodiment, the AR of the AuNR 102 may be in the range of about 0.3-30, and the length and diameter of the AuNR 102 may be in the range of about 3.6-360 nanometer (nm) and about 1.2-120 nm, respectively. In one embodiment, the AR of the AuNR 102 is in the range of about 1-9. In one embodiment, the precise AR of the AuNR 102 is in the range of about 2-5. In one embodiment, the precise AR of the AuNR 102 is in the range of about 2.77-3.23, or about 3±0.23. In one embodiment, the length and diameter of the AuNR 102 may be in the range of about 10-100 nm and about 1-40 nm, respectively. In one embodiment, the particle length and diameter of the AuNR 102 may be approximately 36±0.80 nm and 12±0.41 nm, respectively. In one embodiment, these two dimensions are adequate to form two kinds of surface plasmon modes: a weak one around 520 nm transvers mode, and a very strong longitudinal plasmon around 766 nm [26]. The longitudinal surface plasmon is crucial, and the maximum excitation of this strong surface plasmon mode can be achieved when excited by a Raman excitation laser at about 784 nm. This ensures ultimate sensitivity and very low detection limits when uses SERS for cancer cell detection.

In one embodiment, the shell 106 is a silver layer. The silver layer 106 is coated on the AuNR 102 to form a silver coated gold nanorod (AuNR/Ag). In one embodiment, the AuNR 102 and the silver layer 106 have rough surfaces.

In one embodiment, the thickness of the silver layer 106 may be in the range of about 0.2-20 nm. In one embodiment, the thickness of the silver layer 106 is In the range of about 0.5-5 nm. In one embodiment, the thickness of the silver layer 106 is about 1-2 nm. In one embodiment, the thickness of the silver layer 106 is about 1.7 nm. The thin silver layer 106 helps maintain the longitudinal surface plasmon wavelength as close as possible to the excitation laser source (784 nm), in order to achieve the maximum SERS signal. Any thick silver coating will change the surface plasmon significantly [30].

In one embodiment, the reporter layer 110 is a Raman reporter molecule layer having Raman reporter molecules. In one embodiment, the Raman reporter molecules are thiolated organic molecules absorbed on the surface of the AuNR/Ag. In one embodiment, the Raman reporter molecule may be at least one of 4-mercaptobenzoic acid (4MBA), p-aminothiophenol (PATP), p-nitrothiophenol (PNTP), 4-(methylsulfanyl) thiophenol (4MSTP), and other molecules with unique Raman spectra and intense Raman peak intensities. In other words, the one or more nanocomposites 100 of the nanoagent may include at least one of the following four types of nanocomposites: a nanocomposite having a 4MBA reporter layer, a nanocomposite having a PATP reporter layer, a nanocomposite having a PNTP reporter layer, and a nanocomposite having a 4MSTP reporter layer. In certain embodiments, the nanoagent may include all of these four types of nanocomposites 100. All the SER Raman spectra are obtained through the detection of those Raman reporter molecules.

In the above embodiment, the reporter molecule is a Raman reporter molecule. In certain embodiments, the reporter layer 110 may include other type of reporter molecules such that the produced nanoagent may be used together with detecting methods other than SERS, such as MRI, x-ray radiography, CT or IR. In certain embodiments, the reporter molecule is detectable by different methods. In certain embodiments, the report molecules may include one or more fluorescent agents. The one or more fluorescent agents can be quantum dots or fluorescent dyes.

In the above embodiment, the nanoagent includes at least one of the four types of nanocomposites corresponding to four types of reporter molecules. In certain embodiments, the nanoagent may include all four types of nanocomposites. In certain embodiments, the nanoagent may include one, two, three, or more than four types of nanocomposites, and each type of nanocomposite has a special type of reporter molecule. In other embodiments, one type of nanocomposite may include two or more different types of reporter molecules. In certain embodiments, one type of nanocomposite may also include two, three, four or more types of reporter molecules.

In one embodiment, the binding layer 114 is applied to the surface of the SERS reporter molecule coated AuNR/Ag. In one embodiment, the binding layer 114 is a pegylated layer. In one embodiment, the pegylated layer may include thiolated PEG polymers, for example, at least one of HS-PEG, HS-PEG-COOH and HS-PEG-NHx, which are suitable for being used as SERS tags and are non-toxic. Additionally, the thiolated PEG polymers do not displace Raman reporter molecules, which attach to the surface of gold nanoparticles [40]. In certain embodiments, the x in the HS-PEG-NHx is a positive integer. In one embodiment, x is 1 or 2.

In one embodiment, the pegylated layer 114 includes a mixture of HS-PEG and HS-PEG-COOH, which serves as protective, bio-dispersive and linker to the later conjugated antibodies. In one embodiment, the average molecular weight of the HS-PEG is about 5 kD, and the average molecular weight of the HS-PEG-COOH is about 3 kD. In one embodiment, each nanorod (SERS reporter molecule coated AuNR/Ag) requires about 4,200 molecules to assure complete surface coverage, i.e. each HS-PEG molecule required 0.35 $nm^2$ footprint [39]. The pegylated layer 114 may achieve at least two purposes. First, the pegylated layer 114 protects the nanorods surface and makes the nanocomposite more hydrophilic, and easily disperses the nanocomposite in aqueous medium, for example, biological fluids. Second, the pegylated layer 114 provides a carboxylic terminal on the surface of the SERS reporter molecule coated AuNR/Ag, which is the linker between the SERS reporter molecule coated AuNR/Ag surface and the antibodies that will attached thereon for targeting the target, such as cancer cells.

In certain embodiments, the targeting layer 118 is an antibody layer. The antibody layer 118 includes molecules of a type of antibody which specifically targeting certain cancer cell surface antigen. In one embodiment, the antibody is attached covalently to HS-PEG-COOH (—COOH terminal) and plays a role in the specific SERS nanocomposite delivery to the cancer cells.

In one embodiment, the antibody layer 118 may include molecules of at least one of an anti-EpCAM antibody, an anti-CD44 antibody, an anti-IGF-1 Receptor β antibody, an anti-Keratin 18 antibody, and one or more antibodies specific to the target of interest. In other words, the one or more nanocomposites 100 of the nanoagent may include at least one of the following four types of nanocomposites: the nanocomposite having an anti-EpCAM antibody layer, the nanocomposite having an anti-CD44 antibody layer, the nanocomposite having an anti-IGF-1 Receptor β antibody layer, and the nanocomposite having an anti-keratin 18 antibody layer. In one embodiment, the biocompatible nanoagent having at least one of the four types of nanocomposites may be used for detecting and imaging breast cancer cells, for example, MCF-7, and allow for the capability to distinguish one single cancer cells among normal cells. In one embodiment, the biocompatible nanoagent includes all four types of nanocomposites.

In the above embodiment, the targeting layer 118 includes antibodies. In certain embodiments, the targeting layer 118 may include other type of targeting molecules to specifically binding an object, for example, a ligand that can bind a receptor, or a lectin that can bind a carbohydrate.

In certain embodiments, the nanocomposite may further include one or more molecules of interest attached to the binding layer 114 or the targeting layer 118. In one embodiment, the molecule of interest is a growth factor that induces certain biological functions, including the growth, proliferation of differentiation of cells or organisms. In one embodiment, the molecule of interest is a protein, a drug, or a biological system that induces certain biological functions, the death of cells, tissues, or organisms. The one or more drugs may be anticancer drugs, antibiotics, or antiviral drugs.

In the above embodiment, the nanoagent may include at least one of the four types of nanocomposites corresponding to four types of reporter molecules. In certain embodiments, the nanoagent may include all four types of nanocomposites. In certain embodiments, the nanoagent may include one, two, three, or more than four types of nanocomposites, and each type of nanocomposite has a special type of reporter molecule. In other embodiments, one type of nanocomposite may include two or more different types of reporter molecules.

In the above embodiment, the nanoagent includes at least one of the four types of nanocomposites corresponding to four types of antibodies. In certain embodiments, the nanoagent may include all four types of nanocomposites. In certain embodiments, the nanoagent may include one, two, three, or more than four types of nanocomposites, and each type of nanocomposite has a specific type of antibody. In other embodiments, one type of nanocomposite may include two or more different types of antibodies.

In one embodiment, the nanoagent as described above can be used to detect at least one tumor cell or at least one pathogen by SERS. In one embodiment, the tumor cell is a circulating tumor cell.

In certain embodiments, the nanocomposite of the nanoagent may further include one or more molecules of interest attached to the nanocomposite. In one embodiment, the molecule of interest is a growth factor that induces certain biological functions, including the growth, proliferation of differentiation of cells or organisms. In one embodiment, the molecule of interest is a protein, a drug, or a biological system that induces certain biological functions, the death of cells, tissues, or organisms. The one or more drugs may be anticancer drugs, antibiotics, or antiviral drugs.

In other embodiments, the nanoagent is configured to detect a target of interest other than at least one tumor cell, or configured to be used with methods other than SERS. In one embodiment, the nanoagent is configured to detect a specific type of cell, for example a cancer cell, a blood and immune system cell, a hormone secreting cell, or any other cells that express a specific antigen or certain cell surface molecules. In one embodiment, the nanoagent is configured to detect a pathogen, for example a bacteria, a fungus or a virus. In one embodiment, the nanoagent is configured to detect an exogenous chemical or device that is applied to a patient. In one embodiment, the detection using the nanoagent can be performed in vivo or in vitro.

In one embodiment, the nanoagent includes Raman reporter molecules that are detectable by SERS. In certain embodiment, the nanoagent may include reporter molecules detectable by methods other than SERS, such as MRI, x-ray radiography, CT, or IR. The nanoagent is therefore configured to be applied with methods other than SERS, for specific targeting, detection, and treatment of cancer cells or other targeted cells, tissues or objects. In certain embodiments, the reporter molecules are detectable by two, three, four or more different methods described above. In certain embodiments, the report molecules may include one or more fluorescent agents. The one or more fluorescent agents can be quantum dots or fluorescent dyes.

In another aspect, the present invention is directed to a process for making a biocompatible nanoagent. In certain embodiments, the biocompatible nanoagent may have the structure as shown in FIG. 1.

Figure 2A:
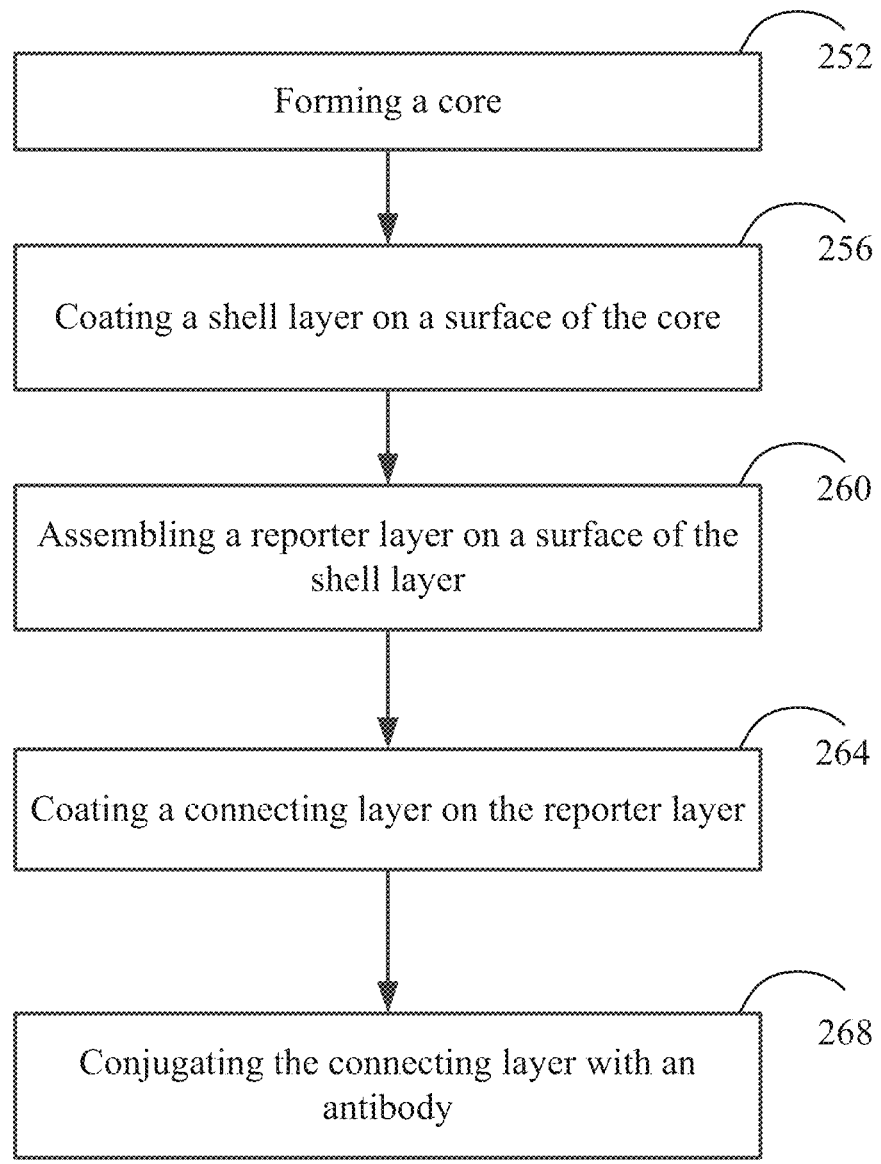
FIG. 2A shows a flowchart of producing nanocomposites of a nanoagent according to one embodiment of the invention.
Figure 2B:
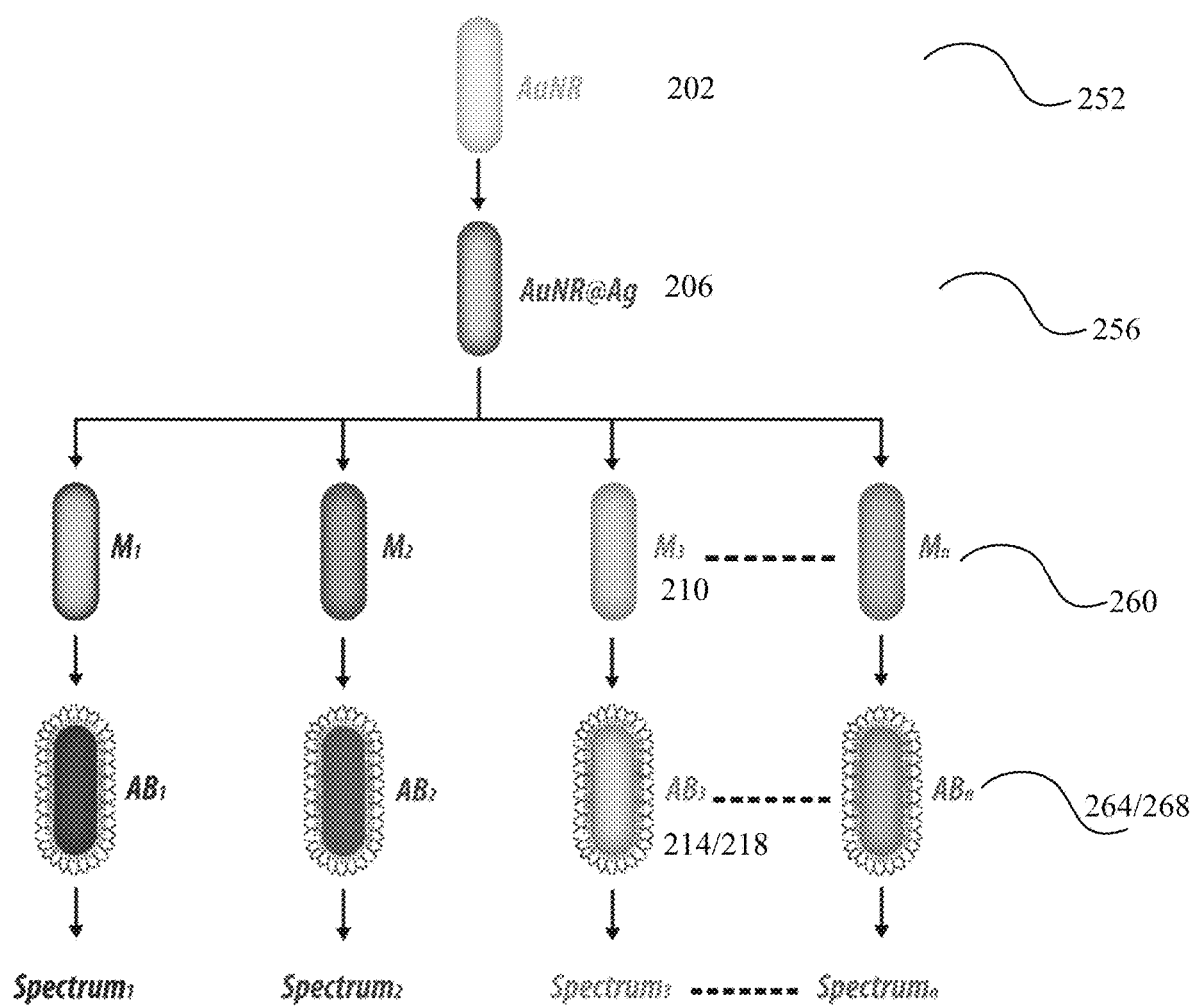
FIG. 2B schematically shows a process of producing nanocomposites of a nanoagent according to one embodiment of the invention.

FIG. 2A shows a flowchart of producing nanocomposites of a nanoagent according to one embodiment of the invention. FIG. 2B schematically shows a process of producing nanocomposites of a nanoagent according to one embodiment of the invention. Referring to FIGS. 2A and 2B, the process of producing nanocomposites includes a plurality of operations. At operation 252, a core (e.g., the AuNR 202) is formed. At operation 256, a shell layer (e.g., the silver layer 206) is wrapped around the core (e.g., the AuNR 202) to form the AuNR/Ag. At operation 260, a reporter layer 210 (e.g., M1, M2, M3 or M4) is assembled or coated on the surface of the shell layer (e.g., the silver layer 206). At operation 264, a binding layer 214 (e.g., the pegylated layer) is coated on the reporter layer 210, and at operation 268, a targeting layer 218 (e.g., the antibody layer) is attached on the binding layer 214.

As discussed above, the core 202 being prepared in operation 252 may be the AuNR. In one embodiment, the AuNR 202 with tuned size is prepared according to the seed mediated method by Nikoobakht [26]. Specifically, 5 ml of 0.2 M hexadecyltrimethylammoniumbromide (CTAB) solution is mixed with 5 ml of 0.0005 M $HAuCl_4$, and then 600 μl of $NaBH_4$ is added to the mixture with stirring for about two minutes, to form a seed solution. To synthesize AuNRs with an aspect ratio around 3, 5 ml of 0.2 M CTAB is mixed with 150 μl of 0.004 M silver nitrate solution to form a first mixture. Then, 5 ml of 0.001 M $HAuCl_4$ is added to and mixed with the first mixture to form a second mixture. After that, 70 μl of 0.0788 M ascorbic acid is mixed with the second mixture to form a third mixture. Finally, 12 μl of the prepared seed solution is added to the third mixture to form a fourth mixture. The fourth mixture is kept at 30° C. for about 40 minutes without any further stirring to form the AuNRs.

Figure 3:
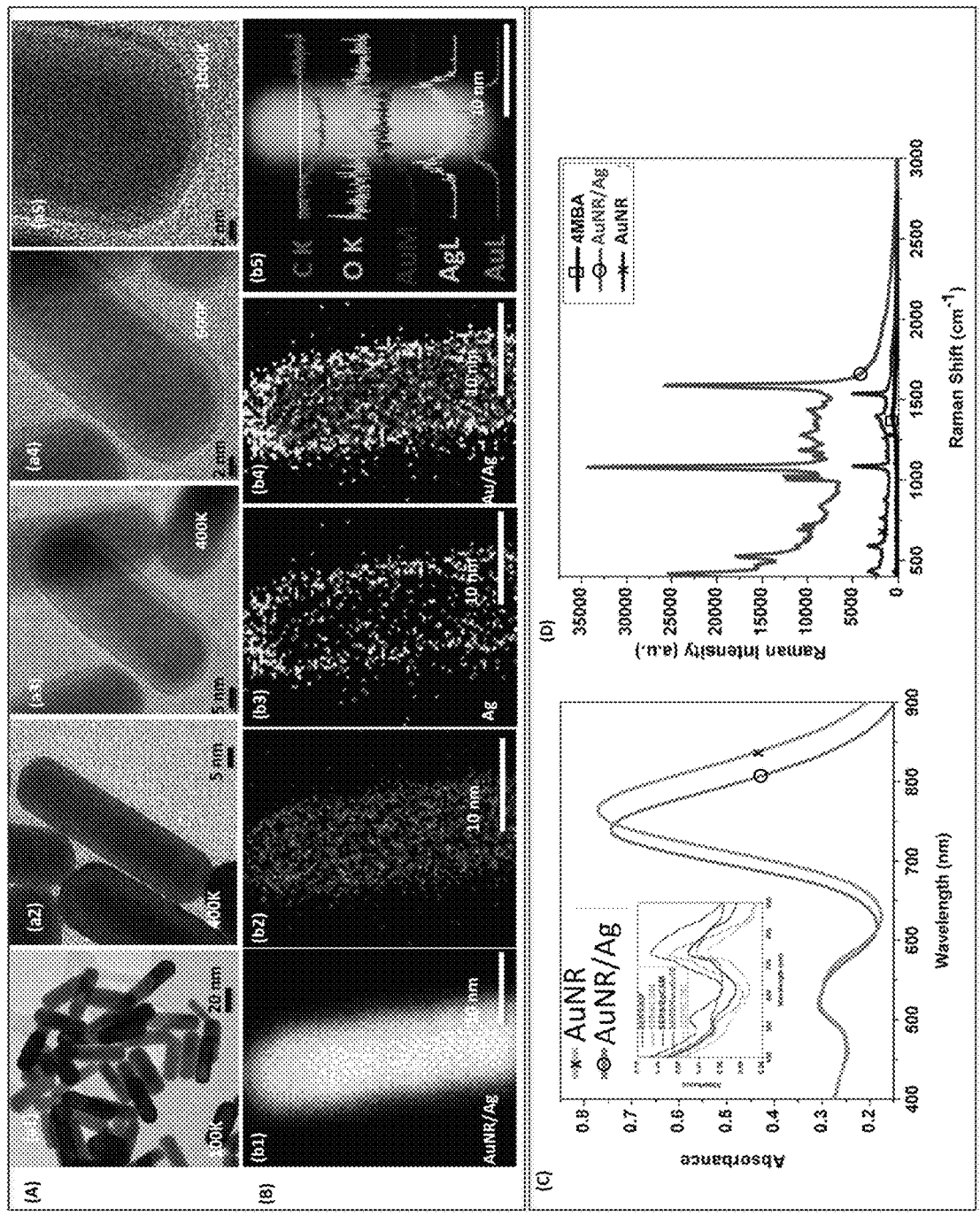
FIG. 3 shows images and diagrams of gold nanorods, silver coated gold nanorods, and nanocomposites according to certain embodiments of the present invention, where (A) shows HRTEM images of gold nanorods and silver coated gold nanorods according to certain embodiments of the present invention; (B) shows SEM and STEM images of a silver coated gold nanorod according to one embodiment of the present invention; (C) shows UV-Visible spectra of gold nanorods and silver coated gold nanorods according to one embodiment of the present invention; and (D) shows Raman signal intensity of gold nanorods, silver coated gold nanorods and nanocomposites having 4MBA according to one embodiment of the present invention.

FIG. 3 (A) shows HRTEM images of gold nanorods and silver coated gold nanorods according to certain embodiments of the present invention, and FIG. 3 (C) shows UV-Visible spectra of gold nanorods and silver coated gold nanorods according to one embodiment of the present invention. As shown by HRTEM images of (a1) and (a2) of FIG. 3 (A), the particle length and diameter of the AuNRs are approximately 36±0.80 nm and 12±0.41 nm, respectively. As shown in FIG. 3 (C), these two dimensions are adequate to form two kinds of surface plasmon modes: a weak one around 520 nm transvers mode, and a very strong longitudinal plasmon around 766 nm [26]. As discussed above, the longitudinal surface plasmon is crucial, where the maximum excitation of this strong surface plasmon mode with the excitation by a Raman excitation laser at 784 nm can be achieved. This ensured achieving ultimate sensitivity and very low detection limits.

As discussed above, the silver layer 206 is coated on the AuNR 202 in operation 256 to form a silver coated gold nanorod (AuNR/Ag). In certain embodiments, the prepared AuNRs are covered with a thin (>1 nm) silver layer, using the reported method [30, 34], which are incorporated by reference in their entireties. Specifically, the AuNRs formed by the operation 252 are purified by centrifugation (10,000 rpm, 30 min) twice to remove any excess reagents, using an ultracentrifuge (Thermo Scientific, Sorvall RC6+) with the rotor F215-8X50Y. The precipitate is re-dispersed in 5 ml CTAB solution by sonication. Then, 5 ml of 1% PVP solution and 250 μl of 0.001 M $AgNO_3$ are added to the AuNRs solution with gentle mixing. After that, 100 μl of 0.1 M ascorbic acid is added and 200 μl of NaOH solution is added to elevate the pH to around 9, in order to initiate the silver ion reduction reaction, such that silver coated gold nanorods are formed.

As discussed above, the thin silver layer 106 helps maintain the longitudinal surface plasmon wavelength as close as possible to the excitation laser source (784 nm), in order to achieve the maximum SERS signal. As shown by HRTEM images of (a3) to (a5) of FIG. 3A, the thickness of the silver layer 206 is about 1.7 nm. Any thick silver coating will change the surface plasmon significantly [30]. FIG. 3(D) shows Raman signal intensity of gold nanorods, silver coated gold nanorods and nanocomposites having 4MBA according to one embodiment of the present invention. Specifically, FIG. 3(D) shows role of silver layer in SERS Raman enhancing (acquisition time 10 s). As shown in FIG. 3(D), the silver layer 106 enhances the SERS Raman signal of AuNR/Ag by a factor of at least 129 times compared to that of pure AuNR. The calculation of the enhancement factor was done by analyzing the Raman intensity of the same peaks when the Raman molecule (4MBA) was deposited on the gold nanorods and on the AuNR/Ag nanostructures, as shown in FIG. 3D.

FIG. 3(B) shows SEM and STEM images of a silver coated gold nanorod according to one embodiment of the present invention. As shown in FIG. 3(B), (b1) is a SEM image of a AuNR/Ag, (b2) is a STEM gold EDS element image of the AuNR/Ag, (b3) is a STEM silver EDS layer element image of the AuNR/Ag, (b4) is a STEM overlapped image of the AuNR/Ag, and (b5) is a EDS cross-scanning spectra of the AuNR/Ag.

Referring back to FIG. 3(C), the silver layer epitaxial growth on the gold nanorod surface can be confirmed by the absorbance spectra. Upon the silver layer growth, the longitudinal band of gold nanorods showed a blue shift of around 20 nm (to about 740 nm), and there were no significant silver band appeared in the lower wavelength, which supposes to appear in that range if the silver completely covered the gold nanorods. This result is consistent with the HRTEM images that a very thin layer of silver has formed on the gold nanorod surface. The thin silver layer 206 helps maintain the longitudinal surface plasmon wavelength as close as possible to the excitation laser source (784 nm), in order to achieve the maximum SERS signal. Any thick silver coating will change the surface Plasmon significantly [30]. Further, the inserted figure in FIG. 3 (C) shows the UV-Visible spectra of four types of nanocomposites having Anti-EpCam antibody, anti-CD44 antibody, anti-keratin 18 antibody, anti-IGF-I antibody, and a negative control nanocomposite having anti-CD45 antibody, according to one embodiment of the present invention. As shown in the inserted UV-Visible spectra, after the bioconjugation of the different types of antibodies on the surface of the silver-gold nanorod, there was still strong absorption in the UV-Visible spectra for both longitudinal and transversal absorbance.

As discussed above, the reporter layer 210 is coated on the silver layer 206 in operation 260. In certain embodiments, the reporter layer 210 may be a Raman reporter molecule layer, and the Raman reporter molecules may be thiolated organic molecules absorbed on the surface of the AuNR/Ag. The thiolated Raman reporter molecules are more easily assembled on the silver surface rather than gold [38] by forming Ag—S covalent bond within a short period of time, for example about 3 hours, and at moderate temperature, for example ≥45° C. In certain embodiments, different reporter molecules or marker molecules may be used. The AuNR/Ag assembled with reporter or marker molecules can be named, $M_1, M_2, M_3, \ldots, M_n$, respectively, which includes the different reporter or marker molecules, where n is a positive integer. Specifically, the silver coated gold nanorods (AuNR/ Ag) obtained in the operation 256 may be purified by centrifugation at 12,000 rpm and redispersed in deionized (DI) water. The centrifugation may be repeated at least once to remove any excess reagents. Then thiophenol molecules can be self-assembled on the surface of silver layer [45]. In one example, five thiophenol derivatives are prepared with 10 mM each ethanol based solution, in five separate conical flasks each contain 5 ml of AuNR/Ag. Then 5 µl of one of 4MBA, PATP, PNTP, 4MSTP, and 4ADPS is added and kept under stirring for about 3 hours with 45° C. to assure that a large portion of surface attached CTAB are replaced by Raman SERS molecules. Unabsorbed excess was removed by centrifugation once at 10,000 rpm for 30 min.

As described above, in order to reduce the risks of false results that may raise from using single SERS nanocomposite (one Raman peak signal), multiple SERS nanocomposites can be simultaneously prepared to have a series of discriminated peaks each corresponds to a specific SERS nanocomposite.

Figure 4:
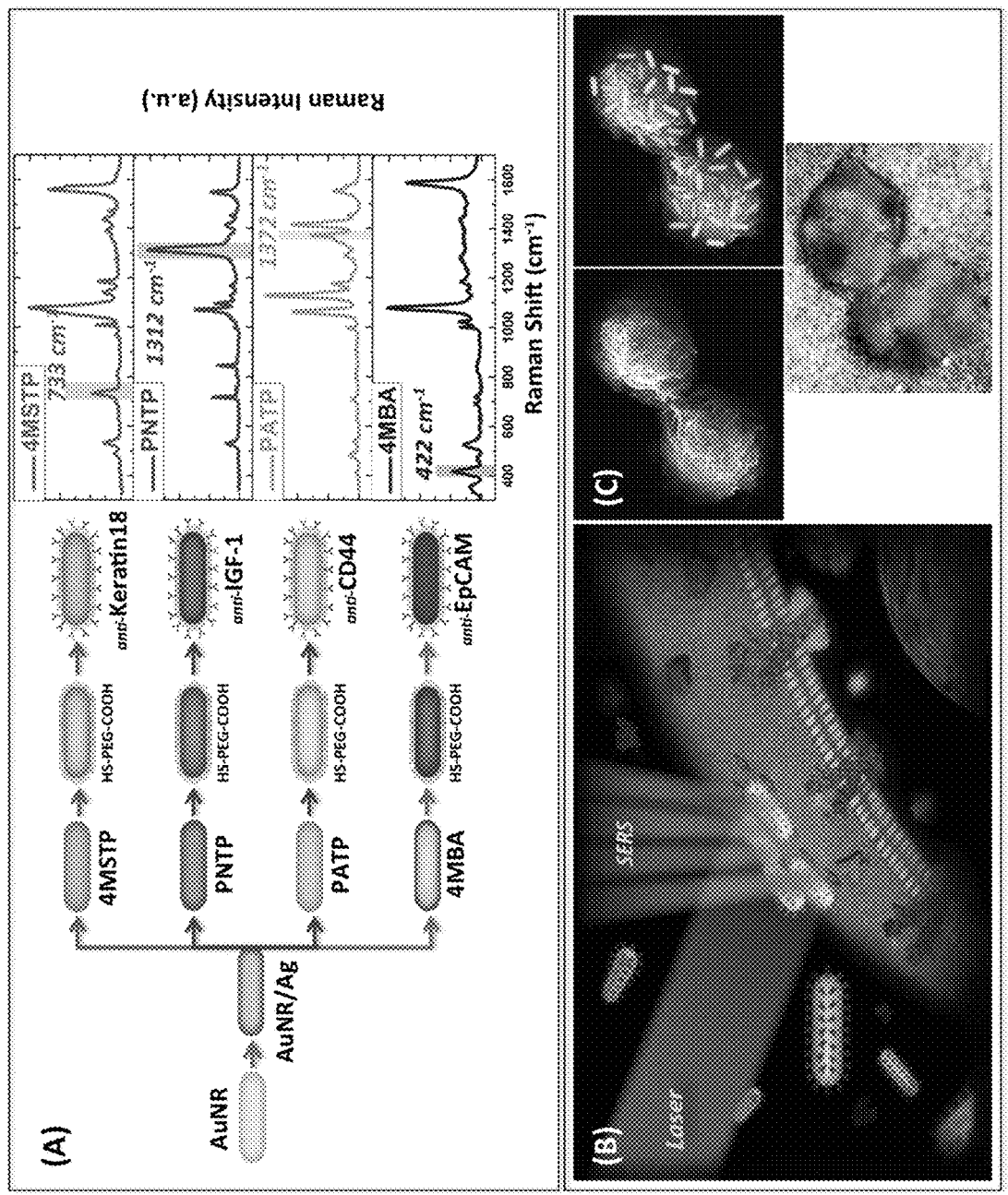
FIG. 4 schematically shows diagrams of preparing and using different types of SERS nanocomposites for cancer cells detection according to certain embodiments of the invention, where (A) shows a schematic diagram of preparing four types of SERS nanocomposites and the Raman spectra (acquisition time 50 seconds) corresponding to each of the four types of SERS nanocomposites according to one embodiment of the present invention; (B) shows schematically nanocomposites specifically targeting the surface of a breast cancer cell to obtain the SERS thermal spectra according to one embodiment of the present invention; and (C) shows schematic views that different types of SERS nanocomposites accumulate on the surface of breast cancer cells (MCF-7) and produce multi-color spectra according to one embodiment of the present invention.

FIG. 4 schematically shows diagrams of preparing and using different types of SERS nanocomposites for cancer cells detection according to certain embodiments of the invention. Specifically, FIG. 4 (A) shows a schematic diagram of preparing four types of SERS nanocomposites and the Raman spectra (acquisition time 50 seconds) corresponding to each of the four types of SERS nanocomposites according to one embodiment of the present invention. Referring to FIG. 4 (A), schematic diagram of preparing four types of SERS nanocomposites and the Raman spectra (acquisition time 50 s) corresponding to each of the four types of SERS nanocomposites are provided. Each color represents a unique AuNR/Ag covered by small organic compounds then a layer of HS-PEG-COOH and then a specific cancer cell antibody layer, where the blue color represents AuNR/Ag/4MBA/anti-EpCAM, the red color represents AuNR/Ag/PNTP/anti-IGF-1 Receptor β, the green color represents AuNR/Ag/PATP/anti-CD44, and the magenta color-represents AuNR/Ag/4MSTP/anti-Keratin 18. The nanocomposites containing 4MBA shows a specific peak at 422 $cm^{-1}$, the nanocomposites containing PATP shows a specific peak at 1372 $cm^{-1}$, the nanocomposites containing PNTP shows a specific peak at 1312 $cm^{-1}$, and the nanocomposites containing 4MSTP shows a specific peak at 733 $cm^{-1}$. Thus, in one embodiment, four different SERS signals are completely separated and do not have any overlapping peaks.

FIG. 4 (B) shows schematically nanocomposites specifically targeting the surface of a breast cancer cell to obtain the SERS thermal spectra according to one embodiment of the present invention.

FIG. 4 (C) shows schematic views that different types of SERS nanocomposites accumulate on the surface of breast cancer cells (MCF-7) and produce multi-color spectra according to one embodiment of the present invention.

As described above, in one embodiment, the Raman reporter molecule is at least one of 4MBA, PATP, PNTP, 4MSTP, and other molecules with unique Raman spectra and intense Raman peak intensities. In one embodiment, the produced nanocomposites include at least one of a nanocomposite having a 4MBA layer, a nanocomposite having a PATP layer, a nanocomposite having a PNTP layer, and a nanocomposite having a 4MSTP layer. All the SER Raman spectra are obtained through the detection of those Raman reporter molecules. In this way, Raman reporter molecules can be attached on the thin silver surface, while the silver coated gold nanorod still keeps the high SERS signal enhancement. For example, when the Raman reporter molecule is 4MBA, the 4MBA attached silver coated gold rod shows six times more enhancement than Raman signal in the related art.

In certain embodiments, the reporter molecules are suitable for being detected by methods other than SERS, and the biocompatible agent having one or more nanocomposites are therefore configured to be applied with methods other than SER, for specific targeting, detection, and treatment of cancer cells or other targeted objects. In one embodiment, the report molecules may include one or more fluorescent agents, and the one or more fluorescent agents may be quantum dots or fluorescent dyes.

In operation 264, the binding layer 214 is coated on the reporter layer 210. In one embodiment, the binding layer 214 is a pegylated layer. In one embodiment, the pegylated layer 214 includes a mixture of HS-PEG and HS-PEG-COOH, which serves as protective, bio-dispersive and linker to the conjugated antibodies. Specifically, one of the precipitates from the previous step is redispersed in 2 ml HS-PEG-COOH (MW~3000) solution (2 mg/ml in 2 mM NaCl), and vigorously stirred for 15 min. Then, 1.8 ml of HS-PEG solution (2 mg/ml in 2 mM NaCl) is added and kept in contact with the SERS nanoagents at 5° C. overnight. After that, the unbound thiolated PEG is removed by centrifugation at 4000 rpm for 15 min and redispersed using probe sonication twice. The precipitate for each coated nanorod solution is then re-suspended in 1×PBS (phosphate buffer solution) solution.

As described above, to stabilize the prepared SERS nanocomposites, a thin layer of HS-PEG (5 kD)/HS-PEG-COOH (3 kD) mixture are used, each nanorod required around 4,200 molecules to assure complete surface coverage, i.e. each HS-PEG molecule requires 0.35 $nm^2$ footprint [39]. This layer has to serve two purposes: first, to protect the nanorods surface and to make the SERS nanoagents more hydrophilic and easily disperse in aqueous medium like biological fluids, and second to provide a carboxylic terminal on the surface of the SERS nanoagent, which is the linker between the nanorod surface and the antibodies that will used later for targeting cancer cells. Thiolated PEG polymers are widely used with SERS tags and are well known as non-toxic; additionally, they do not displace Raman reporter molecules, which attach to the surface of gold nanoparticles [40].

In operation 268, a targeting layer 218 is attached on the binding layer 214, so as to form the nanocomposites. The formed nanocomposites may include different antibodies, and can be named correspondingly as $AB_1, AB_2, AB_3 \ldots, AB_n$, respectively.

In one embodiment, a two-step conjugation assay [46] is followed to bind the carboxylated PEG covered nanorods (SERS nanorods) with the corresponding antibody, including an activation step and a conjugation step.

Specifically, in the activation step, 4 ml of purified carboxylated SERS nanorods from the previous step is re-suspended in PBS buffer solution using sonic probe for several minutes. A mixture of NHS and EDC (0.012 g each) is added to the solution and stirred for 15 min. After that, unbound materials are washed off twice using centrifugation at 8000 rpm for 10 min using PBS buffer.

In the conjugation step, the carboxyl-activated nanorods are redispersed in 5 ml PBS buffer solution. To each of the five prepared solutions, the corresponding antibody is added (anti-EpCAM to AuNR/Ag/4MBA, anti-CD44 to AuNR/Ag/PATP, anti-IGF-1 receptor β to AuNR/Ag/PNTP, Keratin 18 to AuNR/Ag/4MSTP, and anti-CD45 to AuNR/Ag/4ADPS) and mixed thoroughly. The reaction solution is stirred for 4 hours at room temperature. After that, the antibody tagged nanorods (SERS nanoagents) are washed and re-suspended in 5 ml 1×PBS solution and kept under −20° C. for later use.

As described above, the formed targeting layer 218 may be an antibody layer. The antibody layer 218 includes antibodies that are specifically targeting certain cancer cell surface antigens. In one embodiment, the antibody are attached covalently with HS-PEG-COOH (—COOH terminal) and plays a role in the specific SERS nanocomposite delivery to the cancer cells. In one embodiment, the antibody layer 218 includes at least one of anti-EpCAM antibody, anti-CD44 antibody, anti-IGF-1 Receptor β antibody, anti-Keratin 18 antibody, and one or more antibodies specific to the target of interest.

In certain embodiments, the method further includes attaching one or more molecules of interest to the binding layer 214 or the targeting layer 218. In one embodiment, the molecule of interest is a growth factor that induces certain biological functions, including the growth, proliferation of differentiation of cells or organisms. In one embodiment, the molecule of interest is a protein, a drug, or a biological system that induces certain biological functions, the death of cells, tissues, or organisms. The one or more drugs may be anticancer drugs, antibiotics, or antiviral drugs.

Referring to FIG. 4 (A), schematic diagrams of preparing the four types of SERS nanocomposites and the Raman spectra (acquisition time 50 s) corresponding to each of the four types of SERS nanocomposites are provided. Each color represents a unique AuNR/Ag covered by small organic compounds then a layer of HS-PEG-COOH and then a specific cancer cell antibody layer, where the blue color represents AuNR/Ag/4MBA/anti-EpCAM, the red color represents AuNR/Ag/PNTP/anti-IGF-1 Receptor β, the green color represents AuNR/Ag/PATP/anti-CD44, and the magenta color represents AuNR/Ag/4MSTP/anti-Keratin 18. The nanocomposites containing 4MBA shows a specific peak at 422 $cm^{-1}$, the nanocomposites containing PATP shows a specific peak at 1372 $cm^{-1}$, the nanocomposites containing PNTP shows a specific peak at 1312 $cm^{-1}$, and the nanocomposites containing 4MSTP shows a specific peak at 733 $cm^{-1}$.

In a further aspect, the present invention is directed to a system for at least one target detection by SERS. In certain embodiments, the at least one target includes cancer cells. In certain embodiments, the system includes a nanoagent, a surface-enhanced Raman spectrometer, and a processing unit.

In certain embodiments, the nanoagent may include multiple nanocomposites prepared as described above. The multiple nanocomposites may correspond to SERS signals of multiple colors. In certain embodiments, each nanocomposite may include a silver coated gold nanorod, a Raman reporter molecule layer assembled on the silver layer, a pegylated layer coated on the Raman reporter layer, and an antibody layer conjugated to the pegylated layer, as described above. The nanoagent may be applied, for example, to a blood sample or body fluid sample from a patient or a potential patient. Alternatively, the nanoagent may be applied, for example, by injection, to a patient. Due to the specific targeting property of the antibody on the surface of the nanoagent, the nanoagent may specifically bind to, for example, one or more cancer cells in the blood or other objects. Then an incident radiation signal, e.g., a laser beam, may be applied to the sample/blood/object with the nanoagent, and SERS spectra are collected using the SERS signal from the nanoagent. The collected spectra are processed by the processing unit, such that the presence and/or the quantity of the one or more cancer cells or other targets can be determined.

In certain embodiments, the laser beam for SERS signal excitation may be one beam, or may be split in a multitude of sub-beams. In certain embodiments, the Raman spectra corresponding to the SERS agents could be integrated in a 2D image. Moreover, the laser beam may be off-focused such that the surface of analysis is increased.

In one embodiment, after necessary modification, the system may work with other systems such as DualScan from Horiba or similar systems.

In certain embodiments, the report molecules may include one or more fluorescent agents. The one or more fluorescent agents can be quantum dots or fluorescent dyes. And the system includes an equipment that can be used to detect the one or more fluorescent agents.

In yet another aspect, the present invention is directed to a method of detecting one or more targets, such as cancer cells, by SERS, using the system as described above.

In certain embodiments, the nanocomposite in the above described system may further include one or more molecules of interest for treating the one or more targets. In one embodiment, the molecule of interest is a growth factor that induces certain biological functions, including the growth, proliferation of differentiation of cells or organisms. In one embodiment, the molecule of interest is a protein, a drug, or a biological system that induces certain biological functions, the death of cells, tissues, or organisms. The one or more drugs may be anticancer drugs, antibiotics, or antiviral drugs.

Comparing with the structure and detection method in related art, the biocompatible nanoagent and the method of using the nanoagent for detecting at least one target, such as cancer cells, by SERS according to certain embodiments of the present invention, among other things, has the following advantages.

Firstly, SERS provides a high resolution, high sensitivity detection method over conventional Raman method. Specifically, SERS signals are significant enhanced compared to the conventional Raman signal, allowing signal collection from down to a single molecule level when various noble metals of rough surfaces or nanomaterials are used. The enhancement factors for the Raman-scattering signals of SERS can be more than one million-fold compared with normal Raman signals. Therefore, SERS has a significant potential to be used in bio-medical applications [9].

Secondly, in certain embodiments of the present invention, silver coated gold nanorods (AuNR/Ag) are used to prepare the nanoagent for SERS detection. The AuNR/Ag shows stronger spectroscopic properties compared to AuNR [31] or silver nanoparticles. In one embodiment, metallic nano-silver does not suppress surface plasmons as strongly as nano-gold [31]. Further, the silver-gold interface (AuNR/Ag) core-shells have 40-50% more light scattering capacity compared to pure AuNRs [30], which makes them excellent candidates for SERS bio-medical applications where single molecule level detection limits are required. Accordingly, in certain embodiment, the AuNR/Ag in the nanoagent is superior to gold nanoparticles or silver nanoparticles.

Thirdly, in certain embodiments of the present invention, four different antibodies against specific surface antigens of breast cancer cell line MCF-7 are used for preparing the biocompatible nanocomposite for SERS detection. The four antibodies include Anti-EpCam antibody, anti-CD44 antibody, anti-keratin 18 antibody, and anti-IGF-I antibody. The four corresponding antigens are highly expressed in certain cancer cells, especially breast cancer cells. The four types of antibodies and corresponding SERS reporter molecules can be represented by different colors in SERS detection. When the SERS signals represented by different colors are combined, the multicolor combination shows high sensitivity and accuracy than single color detection, and prevent signal overlapping.

EXAMPLES

Example 1: Preparing a Biocompatible Nanoagent

In all preparation procedures, deionized water (DI water, 18 Ω/cm) was used. The following chemicals were purchased from Sigma-Aldrich and used without further purification: Gold (III) chloride trihydrate (99%), sodium borohydride (99%), L-ascorbic acid (98%), 4-mercaptobenzoic acid (4MBA), p-aminothiophenol (PATP), p-nitrothiophenol (PNTP), 4-methylsulfanylthiophenol (4MSTP), and 4-aminophenyldisulfide (4APDS), Polyvinylpyrrolidone (PVP) (MW ~10,000), N-hydroxysuccinimide (NHS), 1N-ethyl-N'-(3-dimethylaminopropyl) carbodiimide hydrochloride (EDC). Silver nitrate was purchased from Fisher Scientific. Hexadecyltrimethylammoniumbromide (CTAB 99%) was purchased from MP Biomedicals. SH-PEG (Mw ~5000) was purchased from Nanocs (95%). HS-PEG-COOH (Mw ~3000) was purchased from Sigma-Aldrich.

All antibodies used (anti-EpCAM, anti-CD44, anti-CD45, anti-IGF-1 Receptor (3, anti-cytokeratin 18) were purchased from Cell Signaling at high purity.

Human breast carcinoma cell line (MCF7) and fibroblast normal skin cell line were purchased from the American Type Culture Collection (ATCC). Culture media, including culture supplies, were purchased from Fisher Scientific.

In Example 1, the nan-agent according to certain embodiments of the present application was synthesized as follows.

Synthesis of gold nanorods: gold nanorods (AuNRs) with turned size were prepared according to the seed mediated method by Nikoobakht [26]. Briefly, the seed solution was first prepared by mixing 5 ml of 0.2 M CTAB solution with 5 ml of 0.0005 M $HAuCl_4$, and then adding 600 μl of $NaBH_4$ with stirring for two minutes. To synthesize AuNRs with an aspect ratio around 3, 5 ml of 0.2 M CTAB was mixed with 150 μl of 0.004 M silver nitrate solution, then 5 ml of 0.001 M $HAuCl_4$ was added and mixed, after that 70 μl of 0.0788 M ascorbic acid was mixed with the solution and finally 12 μl of seed solution was added. The mixed solution was kept at 30° C. for 40 minutes without any further stirring.

Coating of AuNR with a thin shell silver layer to form a silver coated gold nanorod (AuNR/Ag): the prepared AuNRs were covered with a thin (>1 nm) silver layer, using the previously reported method [30, 44]. AuNRs from the synthesis step were purified by centrifugation (10,000 rpm, 30 min) twice to remove any excess reagents, the precipitate was re-dispersed in 5 ml CTAB solution by sonication, then 5 ml of 1% PVP solution and 250 μl of 0.001 M $AgNO_3$ were added to AuNRs solution with gentle mixing. After that 100 μl of 0.1 M ascorbic acid was added and 200 μl of NaOH solution was added to elevate the pH to around 9, in order to initiate the silver ion reduction reaction.

Assembling SERS compounds on the surface of the AuNR/Ag: the AuNR/Ag from the previous step were purified by centrifugation at 12,000 rpm and redispersed in deionized water, twice to remove any excess reagents. Thiophenol molecules can be self-assembled on the surface of the silver layer [45]. Five thiophenol derivatives were prepared with 10 mM each ethanol based solution, in five separate conical flasks each contain 5 ml of AuNR/Ag. 5 μl of 4MBA, PATP, PNTP, 4MSTP, or 4ADPS were added separately and kept under stirring for 3 hours at 45° C., this step assured that a large portion of surface attached CTAB were replaced by Raman SERS molecules. Unabsorbed excess was removed by centrifugation once at 10,000 rpm for 30 min.

Coating with HS-PEG and HS-PEG-COOH: each precipitate from the previous step was redispersed in 2 ml HS-PEG-COOH (MW~3000, 2 mg/ml in 2 mM NaCl) solution and vigorously stirred for 15 min, then 1.8 ml of HS-PEG (2 mg/ml in 2 mM NaCl) solution was added and kept in contact with the SERS nanoagents at 5° C. overnight. After that, the unbound thiolated PEG was removed by centrifugation at 4,000 rpm for 15 min and redispersed using probe sonication twice. The precipitate for each coated nanorod solution was re-suspended in 1×PBS (phosphate buffer solution) solution.

Conjugation of coated SERS nanorods with antibodies: a two-step conjugation assay [46] was followed to bind the carboxylated PEG covered nanorods (SERS nanorods) with the corresponding antibody.

Activation Step:

4 ml of purified carboxylated SERS nanorods from the previous step was re-suspended in PBS buffer solution using sonic probe for several minutes. A mixture of NHS and EDC (0.012 g each) was added to the solution and stirred for 15 min. After that, unbound materials were washed off twice using centrifugation at 8,000 rpm for 10 min and PBS buffer.

Conjugation Step:

the carboxyl-activated nanorods were redispersed in 5 ml PBS buffer solution. To each of the five prepared solutions, the corresponding antibody was added (anti-EpCAM to AuNR/Ag/4MBA, anti-CD44 to AuNR/Ag/PATP, anti-IGF-1 receptor β to AuNR/Ag/PNTP, Keratin 18 to AuNR/Ag/4MSTP, and anti-CD45 to AuNR/Ag/4ADPS) and mixed thoroughly. The reaction solution was stirred at for 4 hours at room temperature. After that, the antibody tagged nanorods (SERS nanoagents) were washed and re-suspended in 5 ml 1×PBS solution and kept under −20° C. for later use.

Characterization of the Nanoagent Prepared from Example 1

The nanoagents prepared from Example 1 were characterized by variety of method, such as scanning electron microscopy (SEM), transmission electron microscopy (TEM), high resolution TEM (HRTEM), SERS, UV-Vis spectroscopy.

For TEM characterization, the morphology and size of the gold nanorods (AuNRs) according to Example 1 were determined by TEM, JEM-2100F (JEOL USA, Peabody, Massachusetts, USA) with an accelerating voltage of 80 kV. High resolution TEM (HRTEM) imaging was performed at 200 kV. A few drops each of samples suspended in water were deposited on holey-carbon coated copper grids, which were then allowed to dry for 15 minutes on filter papers. The average rod size and the size distribution of each sample were determined by using Image J image analysis tool. The PEG-coated gold nanorod and the protein coated gold nanorod samples were positively stained with 2% uranyl acetate dissolved in 70% ethanol in order to enhance the protein coating layer around the AuNR. The TEM was also equipped with an EDAX Genesis energy dispersive spectroscopy (EDS) of X-ray detection system. Combined with Scanning Transmission Electron Microscopy (STEM), elemental mapping of nanorods can be performed with close to 1 nm lateral resolution. Annular dark field (ADF) imaging under STEM mode was performed with 1.5 nm spot size and 20 cm camera length with a JEOL dark field detector.

For SEM characterization, MCF-7 cells were grown on Thermanox® plastic coverslip (NUNC, Rochester, NY) for 24 hours. Samples were treated with SERS nanoagents for 30 minutes. MCF-7 cells were fixed primarily with 3% glutaraldehyde in 0.1 M phosphate buffer, pH 7.2, followed by a secondary fixative of 2% OsO4 in 0.1 M phosphate buffer. All of the samples were washed thoroughly with 0.1 M phosphate buffer, dehydrated with ascending percentages of ethanol solution, and then dried using Hexamethyldisilazane (HMDS) reagent (EMS, Hatfield, PA). Each dried sample was coated with a thin film of carbon (~3 nm) and visualized under a SEM, JEOL JSM-7000F (JEOL USA, Peabody, Massachusetts) also equipped with an EDAX EDS detection system with an accelerating voltage of 15 kV and a working distance of ~10 mm.

Referring to the HRTEM images as shown in (a1) and (a2) of FIG. 3 (A), the particle length and diameter of the AuNRs are approximately 36±0.80 nm and 12±0.41 nm, respectively. Referring to the HRTEM images as shown in (a1) and (a2) of FIG. 3 (A), the silver film has a thickness of about 1.7 nm.

FIG. 3 (B) shows images of AuNR/Ag, where (b1) is a SEM image, (b2) is a STEM gold EDS element image, (b3) is a STEM silver EDS layer element image, (b4) is a STEM overlapped image, and (b5) is a EDS cross-scanning spectra. The result indicates that the silver atoms give the highest tendency for the outside layer arrangement in this bimetal composition. The thin silver layer helps maintain the longitudinal surface plasmon wavelength as close as possible to the excitation laser source (784 nm), in order to achieve the maximum SERS signal.

Figure 5:
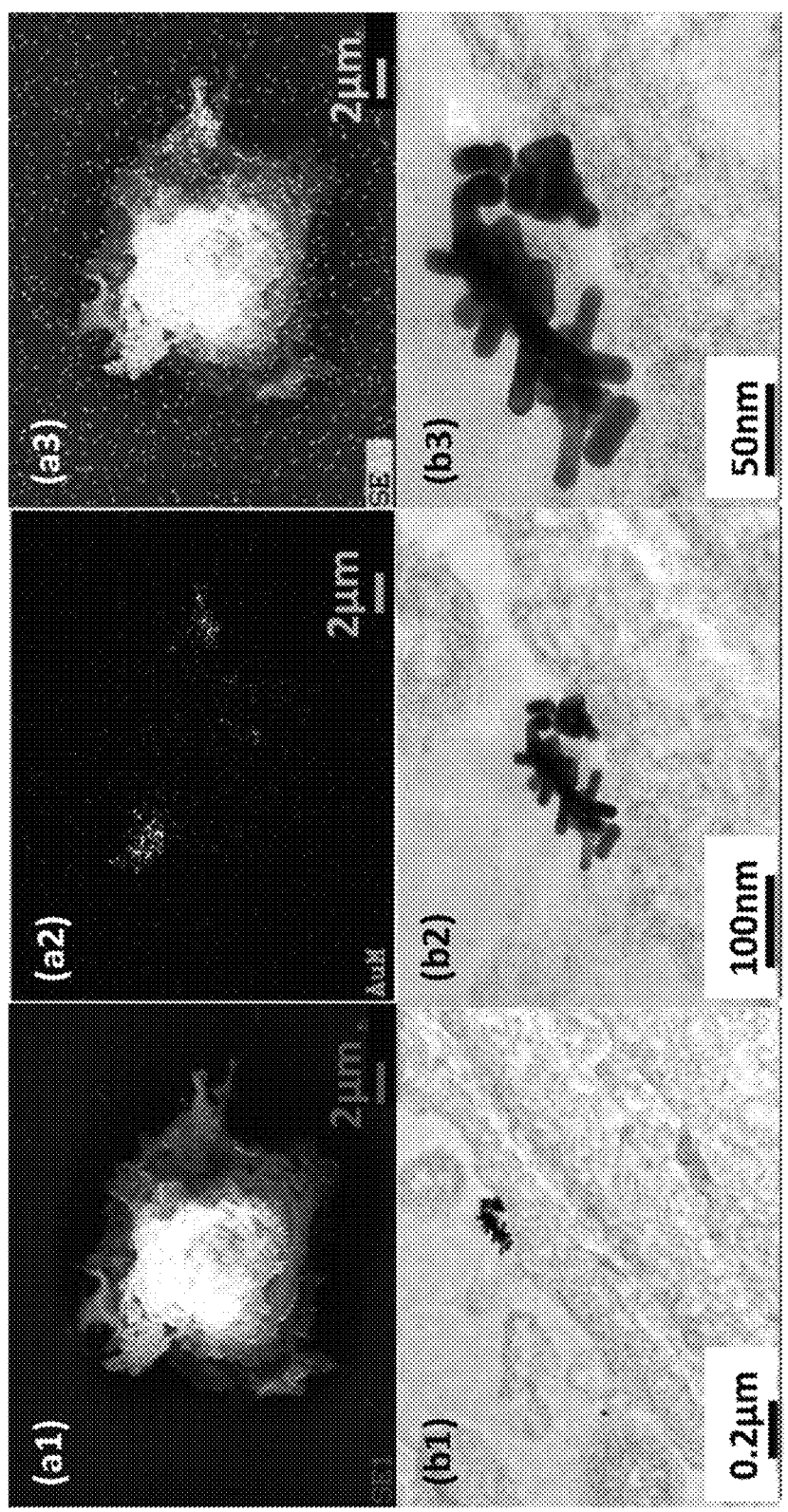
FIG. 5A shows SEM images with EDS elemental analysis of nanocomposites on the MCF-7 cell surface according to one embodiment of the present invention.
FIG. 5B shows TEM images of nanocomposites cluster on the surface of an MCF-7 cell according to one embodiment of the present invention.

FIG. 5A and FIG. 5B show visualization of SERS nanoparticles on the cells' surface, where FIG. 5A shows SEM images with EDS elemental analysis of nanocomposites on the MCF-7 cell surface according to one embodiment of the present invention, and FIG. 5B shows TEM images of nanocomposites cluster on the surface of an MCF-7 cell according to one embodiment of the present invention. As shown in FIG. 5A, (a1) is a SEM image of the nanorods cluster on a MCF7 cell surface, (a2) is an image showing Au EDS elemental analysis of the nanorods cluster, and (a3) is an merged image of the nanorods cluster. As shown in FIG. 5B, (b1), (b2), and (b3) are TEM images of the nanorods (SERS nanoagents) cluster on the surface of an MCF7 cell with different magnification, showing how the nanorods accumulate on the surface of an MCF7 cell. FIGS. 5A and 5B clearly show that the SERS nanoagents accumulated on the surface of the cells.

UV Visible Spectra: 100 µg/ml solution of AuNRs, AuNR/Ag, and all SERS nanoagents were scanned from 400-900 nm using Shimadzu (UV-Visible-NIR) spectrophotometer. The data was re-constructed using software.

FIG. 3 (C) shows UV-Vis spectra of AuNR and AuNR/Ag, and the inserted image shows UV-Vis spectra of SERS nanoagents. As shown in FIG. 3 (C), the two dimensions, particle length and diameter of the AuNRs and AuNR/Ag, are adequate to form two kinds of surface plasmon modes: a weak one around 520 nm transvers mode, and a very strong longitudinal plasmon around 766 nm [26]. The longitudinal surface plasmon is crucial, and the maximum excitation of this strong surface plasmon mode can be achieved when excited by a Raman excitation laser at about 784 nm. This ensures ultimate sensitivity and very low detection limits when uses SERS for cancer cell detection.

Further, the silver layer epitaxial growth on the gold nanorod surface can be confirmed by the absorbance spectra. Upon the silver layer growth, the longitudinal band of gold nanorods showed a blue shift of around 20 nm (to about 740 nm), and there were no significant silver band appeared in the lower wavelength, which supposes to appear in that range if the silver completely covered the gold nanorods. This result is consistent with the HRTEM images that a very thin layer of silver has formed on the gold nanorod surface.

As shown in the inserted image of FIG. 3 (C), after the bioconjugation of the different types of antibodies on the surface of the silver coated gold nanorod, there were still strong absorption in the UV-Vis spectra for both longitudinal and transversal absorbance.

To evaluate the ability of anti-EpCam, CD44, Keratin 18, and IGF-I antibodies to specifically target cancer cells, as well as to discriminate between the two cell lines (MCF-7 and fibroblast), immunocytochemistry techniques were conducted. The antibody binding was identified by the use of a secondary antibody labeling method with four different colors.

Breast adenocarcinoma (MCF-7 cell line), and normal skin fibroblast (BJ-1 cell line) were co-cultured in two-well chamber slides in a density of $15^4$ cells/well with the percentages of 90% fibroblastic BJ-1 cells and 10% cancerous MCF-7 cells. The mixed cells were then incubated for 24 hours for attachment. Post incubation, the cells were washed with 1× of phosphate buffer saline solution 3×5 min each. 200 µl of high purity methanol was added to each well and incubated for 20 min at room temperature for fixation. The methanol was removed, and the cells were washed with 1× of phosphate buffer saline solution 3×5 min each. Subsequently, 200 µl of blocking buffer containing (1×PBS/5% BSA) was added to each well and incubated for 30 min at room temperature. In the meantime, a 1:200 dilution of each antibody-Anti-EpCam, Anti-CD44, Anti-Keratin 18, and Anti IGF-I (Cell Signaling Technology, Boston, Massachusetts)—was prepared using blocking buffer in separate labeled tubes. The blocking buffer was removed, and the diluted antibodies were added to each well and incubated over night at 4° C. The cells were then washed with 1× of phosphate buffer saline solution for 3×5 min each. Four different goat polyclonal secondary antibodies to mouse IgG with different fluorescent properties—Alexa Flour 488, 555, 594, and 647 (abcam, Cambridge, MA)—were used in a dilution of 1:500 with blocking buffer. The secondary antibodies were added to each well and incubated for 1 h in the dark at room temperature. The cells were washed with 1× of phosphate buffer saline solution 3×5 min each, and then 200 µl of 0.5% µg/ml of 4',6-diamidino-2-phenylindole (DAPI) was added and incubated for 5 min at room temperature in the dark to perform nuclear staining. The cells were mounted with mounting medium, covered with the cover slip, and the edges were sealed. Finally, the cells were kept in the dark at 4° C. until examination under the fluorescence microscope using an Olympus BX 51 microscope.

Figure 6:
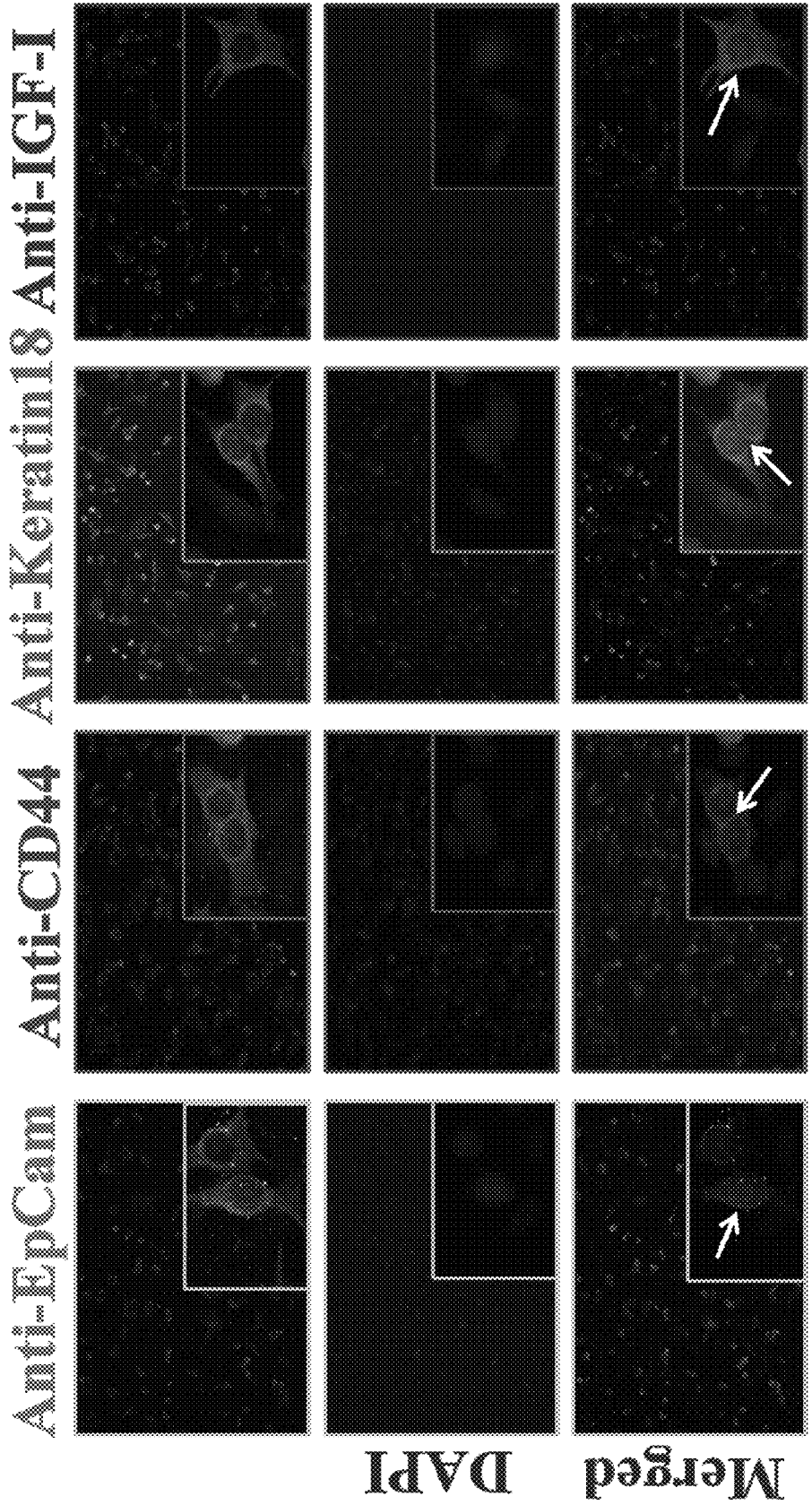
FIG. 6 shows the immunocytochemistry staining (ICC) of MCF-7 cells in mixed culture with fibroblast cells BJ-1 according to one embodiment of the present invention.

FIG. 6 schematically shows the immunocytochemistry staining (ICC) of MCF-7 cells in mixed culture with fibroblast cells BJ-1 according to one embodiment of the present invention. As shown in FIG. 6, the top row shows ICC of cells with anti-EpCAM, anti-CD44, anti-Keratin 18, and anti-IGF antibodies (1:200), respectively, followed by (1:500) goat anti-mouse IgG (Alexa fluor 555, 594, 488, and 647). The middle row shows DAPI nuclear staining of both cell lines. The bottom row shows merged images. The white arrows indicate the presence of antigens localized on the surface of breast cancer cells, and not on the surface of fibroblast cells.

As presented in FIG. 6, the anti-EpCAM antibody, anti-CD44, anti-Keratin 18 and anti-IGF-I were found to selectively bind MCF-7 cancer cells and not to the normal fibroblast cells. As a result, this method could facilitate the specific delivery of SERS nanoagents to breast cancer cells only.

SERS: Referring back to FIG. 3 (D), the silver layer enhances the Raman signal by a factor 129 times (SERS) compared to that of pure AuNR.

Example 2: Using the Prepared Nanoagent for Cancer Cell Detection by SERS

Breast adenocarcinoma (MCF-7 cell line) and skin fibroblast (BJ-1 cells) were purchased from American Type Culture Collection (ATCC). Both cell lines were primarily cultured in 75 cm$^2$ tissue culture flasks and supplemented with the recommended medium—Dulbecco minimum essential medium (DMEM), and Eagle's minimum essential medium (EMEM) respectively, both containing 10% fetal bovine serum (FBS) and 1% penicillin streptomycin (PS), the cells were incubated at 37° C. in humidified incubator and 5% $CO_2$. The medium was changed every 48 h with fresh medium until confluent.

For SERS analysis, mixture of cancerous MCF7 cell line and BJ-1 cell line were seeded in 4 well chamber slides in a density of $10^5$ cells/well and a percentage of 90% BJ-1 cells, 10% MCF-7 cells. The cells were supplemented with complete growth medium and incubated overnight for attachment. After incubation, the medium was interchanged with normal growth medium supplemented by 40 µg/ml of SERS nanoagents (10 µg of each SERS nanoagents) and the cells were further incubated for 30 min at 37° C. The cells were washed for 5 minutes 3 times with 1×PBS, and 2% formaldehyde was added for fixation. After 20 min, the cells were washed 6 times (3 times with 1×PBS, and 3 times with DI water). The cells were left to dry and stored at −20° C. Untreated cells were used as a negative control.

SERS images were collected from the samples using Confocal Raman spectrometer (Horiba Jobin Yvon LabRam HR800, Edison, New Jersey) assembled with He-Ne laser (784 nm) and three Olympus BX-51 lenses with 100× micro-objectives magnitude connected to a Peltier-cooled CCD camera. The spectra were collected using 600-line/mm gratings with the same acquisition time. The spectrometer also has a three-dimensional (3-D) (x-y-z) automatic adjustable stage that can map Raman scanning for a specific area at a minimum distance of 1 In all measurements, the Raman spectrometer was calibrated using the Si—Si Raman signal, which is located at a 521-cm$^{-1}$ Raman shift.

Figure 7A:
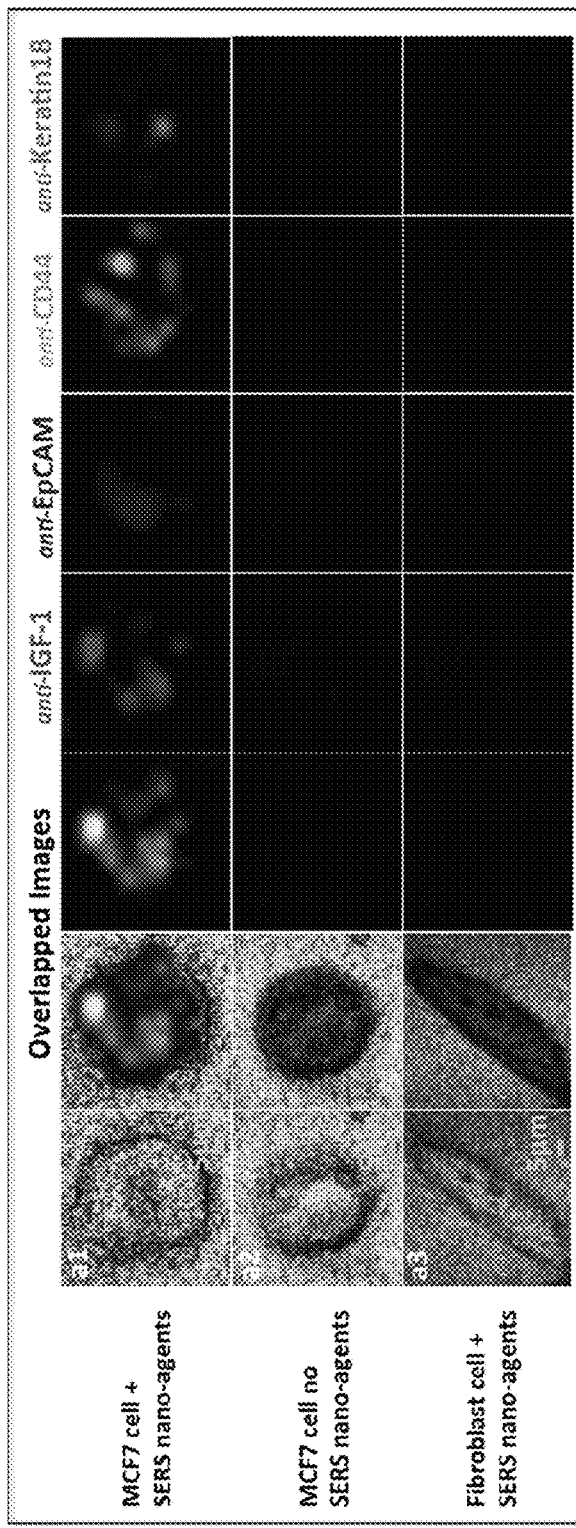
FIG. 7A shows Raman mapping images of cells according to certain embodiments of the present invention, where (a1) shows Raman mapping images for targeting a single MCF-7 cancer cell among fibroblast cells with four different SERS nanoagents; (a2) shows Raman mapping images of a cancer cell without using any SERS nanoagents; and (a3) shows Raman mapping images of a fibroblast cell (normal cell) with four SERS nanoagents.

FIG. 7A shows Raman mapping images of cells according to embodiments of the present invention, where (a1) shows Raman mapping images for targeting a single MCF-7 cancer cell among fibroblast cells with four different SERS nanoagents; (a2) shows Raman mapping images of a cancer cell without using any SERS nanoagents; and (a3) shows Raman mapping images of a fibroblast cell (normal cell) with four SERS nanoagents. As shown in FIG. 7A, normal cells as shown in (a3) and MCF-7 cells without SERS nanoagent have not reveal any Raman signal in scanned regions. These Raman mapping images have clearly confirmed that multiple SERS nanocomposites (blue, red, green, and magenta referred to 4MBA, PNTP, PATP, 4MSTP respectively) of a nanoagent are simultaneously targeting the same MCF-7 cell within 30 minutes of incubation with 8 s Raman acquisition time.

In order to detect the cancer cell MCF-7 in real blood or separated white blood cells, a few of cancer cells (5, 50, 500 or 5000 cells) spiked with (100 µL) whole blood or the separated white blood cell solution. In one embodiment, the two samples (separated blood and whole blood) contain about 50 cancer cells in 7 million white blood cells. Then 50 µg/ml of SERS nanoagents mixture were added to incubate for 30 minutes.

Figure 7B:
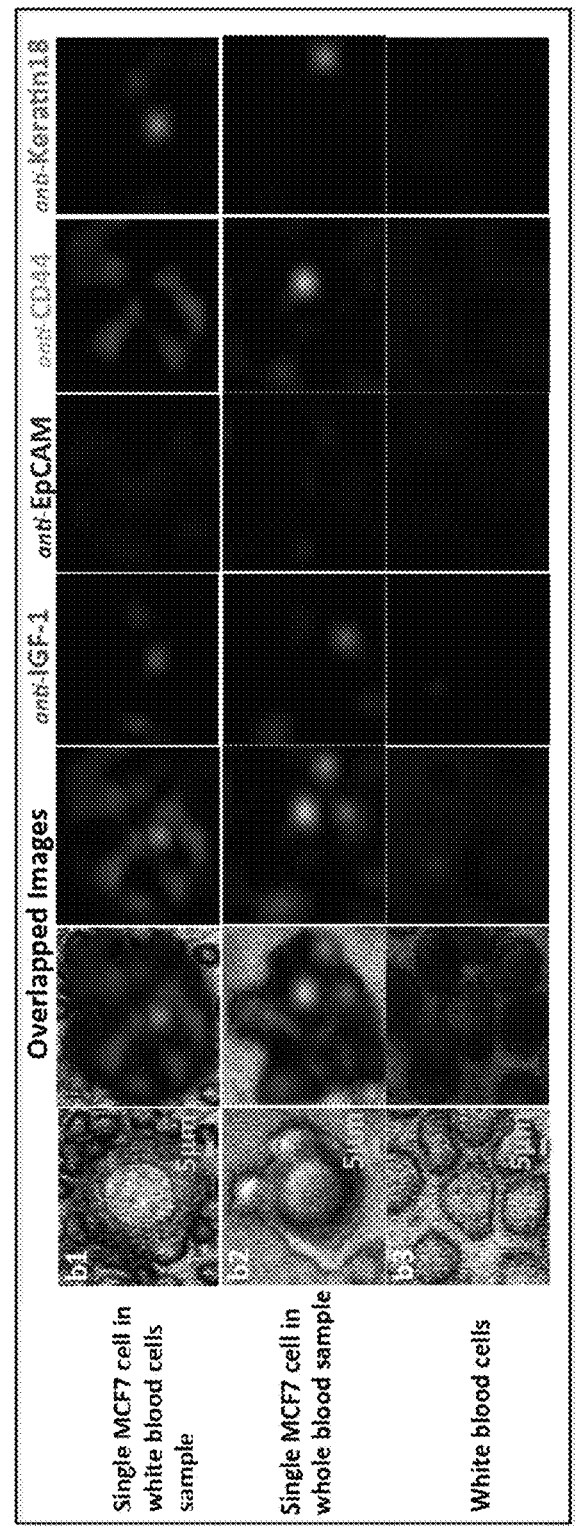
FIG. 7B shows Raman mapping images of cells according to certain embodiments of the present invention, where (b1) shows Raman mapping images of a single cancer cell, MCF-7, among millions of white blood cells, using a nanoagent having four types of nanocomposites; (b2) shows Raman mapping images of a single cancer cell, MCF-7, among millions of whole blood cells, using a nanoagent having four types of nanocomposites; and (b3) shows SERS mapping signal collected from the white blood cells only, i.e., without presence of cancer cells, using a nanoagent having four types of nanocomposites.

FIG. 7B shows Raman mapping images of cells according to certain embodiments of the present invention, where (b1) shows Raman mapping images of a single cancer cell, MCF-7, among millions of white blood cells, using a nanoagent having four types of nanocomposites; (b2) shows Raman mapping images of a single cancer cell, MCF-7, among millions of whole blood cells, using a nanoagent having four types of nanocomposites; and (b3) shows SERS mapping signal collected from the white blood cells only, i.e., without presence of cancer cells, using a nanoagent having four types of nanocomposites. As shown in (b1) and (b2) of FIG. 7B, four different colors show the four different SERS nanoagents were detected in the same cell which were located in the different place of the cancer cell surface and some were overlapped each other. However, signals from the four types of SERS nanocomposites can be distinguish because of the colors, which means the specific Raman peaks. As shown in (b3) of FIG. 7B, there is no specific Raman signal from the white blood cells.

Figures 7C, 7D:
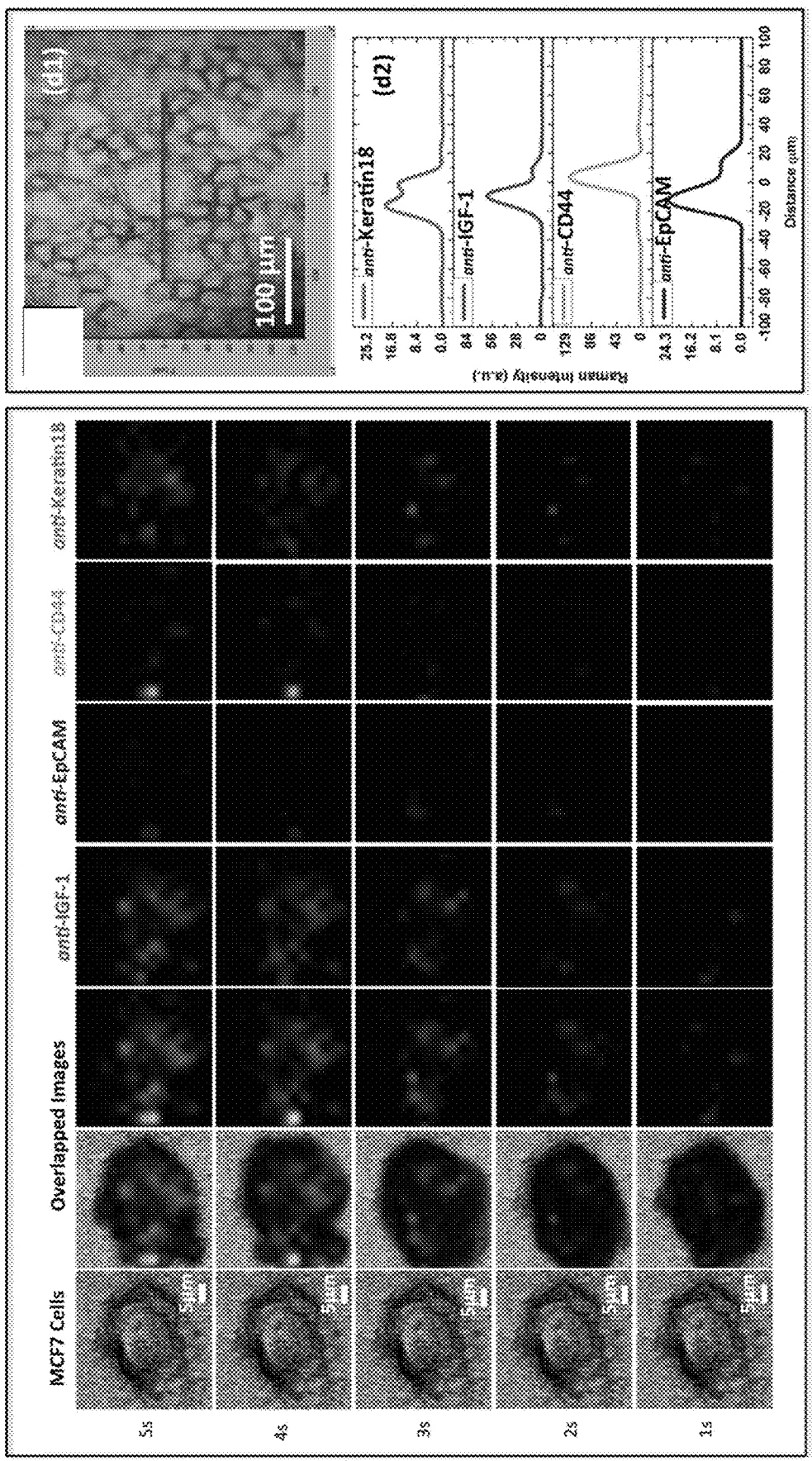
FIG. 7C shows SERS signal collected with different time periods from 1 second(s) to 5 s, using a nanoagent having four types of nanocomposites according to one embodiment of the present invention.
FIG. 7D schematically shows SERS linear scanning position and SERS signal of a selected single cancer cell according to one embodiment of the present invention, where (d1) shows SERS linear scanning position of a selected single cancer cell, and (d2) shows SERS signal of a selected single cancer cell scanned linearly four times along the line in (d1), each time with a specific scanning range corresponding to one of the four types of SERS nanocomposites.

In order to estimate how fast SERS signal could be detected, an MCF7 cell was targeted and scanned several times with different acquisition time (1 s, 2 s, 3 s, 4 s, 5 s). FIG. 7C shows SERS signal collected with different time periods from 1 second(s) to 5 s, using a nanoagent having four types of nanocomposites according to one embodiment of the present invention. As shown in FIG. 7C, SERS signal could be significantly detected mostly within 3 s. The intensity of the Raman signal can be detected variable from 1-8 s depended on the different antibodies of the nanocomposites. The SERS nanoagents having the multiple nanocomposites were successfully targeted on the MCF-7 single cell and detected by Raman among millions of fibroblast cells.

FIG. 7D schematically shows SERS linear scanning position and SERS signal of a selected single cancer cell according to one embodiment of the present invention, where (d1) shows SERS linear scanning position of a selected single cancer cell, and (d2) shows SERS signal of a selected single cancer cell scanned linearly four times along the line in FIG. 7D (d1), each time with a specific scanning range corresponding to one of the four types of SERS nanocomposites. As shown in FIG. 7D, a single cancer cell was selected and scanned linearly four times, each time with a specific scanning range corresponding to that specific SERS nanoagent. FIG. 7D shows that SERS signals come from only the MCF-7 cell and there is no significant signal from the blood cells.

In order to ensure that SERS nanoagent having multiple type of nanocomposites were selectively targeting MCF-7 cells because they are directed to these cells by the antibodies, a negative SERS nanoagent was prepared and tested. Anti-CD45 is a biomolecule known to target white blood cells rather than the MCF-7 cells. The negative SERS nanocomposite of AuNR/Ag/4ADPS/CD45 was prepared and incubated with the same sample of mixed white blood cells and few MCF-7. SERS images were then collected to see if any signal from the cancer cells was received. The results were in complete agreement with our hypothesis, where the SERS signal was obtained from the white blood cells and not from the cancer cells.

Figure 8:
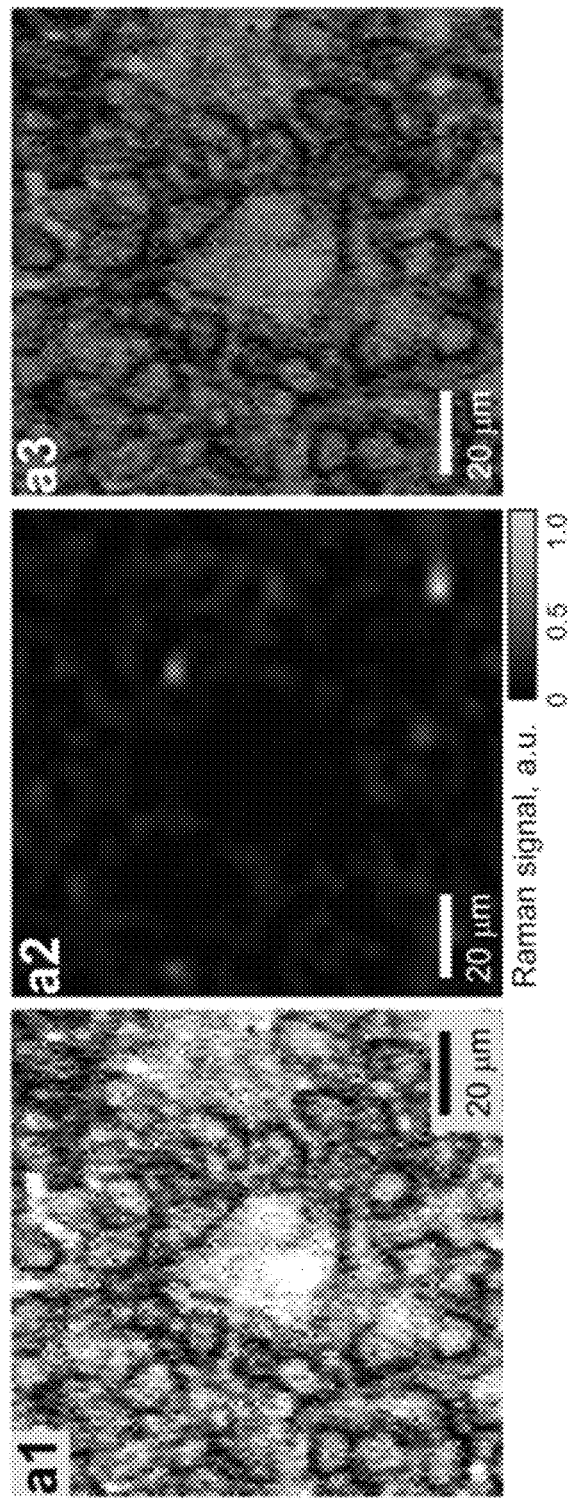
FIG. 8 shows images of SERS signal of a mixture of MCF-7 cell and white blood cells, using the negative nanocomposite having CD45, according to certain embodiments of the present invention.

FIG. 8 shows images of SERS signal of a mixture of MCF-7 cell and white blood cells, using the negative nanocomposite having CD45, according to certain embodiments of the present invention. As shown in (a1) to (a3) of FIG. 8, there was no SERS signal from the MCF-7 cell and all SERS signal coming from the white blood cells, when using the negative nanoagents having CD45.

In summary, according to certain embodiment of the present invention, it is able to detect SERS signals from a single cancer cell among millions of blood cells in a short period of time. The nanostructural agents, formed of four types of silver decorated gold nanorods, were designed to have high optical absorption in the near-infrared region (NIR) and to match the emission of the laser excitation. All four SERS nano-reporters were used for the multicolor superimposed identification of the cancer cells. Each agent, with unique spectral features, was assigned a different color and the identification of the individual cancer cells in blood was performed based on the overlapping of four colors in a 2-dimensional scanning environment. SERS using those nanoagent can successfully detect and image with high resolution a low population of breast cancer cells in peripheral blood or separated white blood cells (for example, 1 in 1 million). Such a multi-spectroscopic approach offers the opportunities of accurate and high sensitivity detection of single cancer cell in blood, given narrow SERS bandwidths of the nano-reporter spectra. Thus, certain embodiments of the present invention provide ultrafast and high specificity detection of the early clinical detection of a multitude of cancer cells or various pathogens in blood.

In the past, CTCs were thought to spread only during the final stages of malignant progression [41, 42]. However, recent researches have demonstrated that CTCs also can be found in the bloodstream during early stages [43]. Consequently, the fast detection of CTCs has become major impact factor for treatment and providing information about the aggressiveness of a tumor, how well patients are responding to treatment, and why some patients do not respond to a specific therapy. Certain methods usually required an enrichment and separation steps of cancerous cells from normal cell which is tedious and time consuming procedures [41]. However, comparing with related art, the present invention, for the first time, is able to detect a single cancer cell (CTC) quickly and within 1 to 7 million of blood erythrocytes cells without any enrichment assay.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims as well as the invention including drawings.

REFERENCES

[1]. Alivisatos, P. The use of nanocrystals in biological detection. *Nat Biotech* 22, 47-52 (2004).

[2]. Michalet, X. et al. Quantum Dots for Live Cells, in Vivo Imaging, and Diagnostics. *Science* 307, 538-544 (2005).

[3]. Nima, Z. A. et al. Single-walled carbon nanotubes as specific targeting and Raman spectroscopic agents for detection and discrimination of single human breast cancer cells. *Journal of Biomedical Optics* 18, 055003-055003 (2013).

[4]. Karmakar, A. et al. Raman spectroscopy as a detection and analysis tool for in vitro specific targeting of pancreatic cancer cells by EGF-conjugated, single-walled carbon nanotubes. *Journal of Applied Toxicology*, n/a-n/a (2011).

[5]. Ferreira, C. S. M. et al. DNA aptamers against the MUC1 tumour marker: design of aptamer-antibody sandwich ELISA for the early diagnosis of epithelial tumours. *Analytical and Bioanalytical Chemistry* 390, 1039-1050 (2008).

[6]. Gao, X., Cui, Y., Levenson, R. M., Chung, L. W. K. & Nie, S. In vivo cancer targeting and imaging with semiconductor quantum dots. *Nat Biotech* 22, 969-976 (2004).

[7]. Liu, Z. et al. In vivo biodistribution and highly efficient tumour targeting of carbon nanotubes in mice. *Nat Nano* 2, 47-52 (2007).

[8]. Weissleder, R., Kelly, K., Sun, E. Y., Shtatland, T. & Josephson, L. Cell-specific targeting of nanoparticles by multivalent attachment of small molecules. *Nat Biotech* 23, 1418-1423 (2005).

[9]. Munro, C. H., Smith, W. E., Armstrong, D. R. & White, P. C. Assignments and Mechanism of SERRS of the Hydrazone Form for the Azo Dye Solvent Yellow 14. *The Journal of Physical Chemistry* 99, 879-885 (1995).

[10]. Zhang, Y., Hong, H., Myklejord, D. V. & Cai, W. Molecular Imaging with SERS-Active Nanoparticles. *Small* 7, 3261-3269 (2011).

[11]. Qian, X. M. & Nie, S. M. Single-molecule and single-nanoparticle SERS: from fundamental mechanisms to biomedical applications. *Chemical Society Reviews* 37, 912-920 (2008).

[12]. Schlücker, S. SERS Microscopy: Nanoparticle Probes and Biomedical Applications. *Chemphyschem* 10, 1344-1354 (2009).

[13]. Merchant, B. Gold, the Noble Metal and the Paradoxes of its Toxicology. *Biologicals* 26, 49-59 (1998).

[14]. Root, S. W., Andrews, G. A., Kniseley, R. M. & Tyor, M. P. The distribution and radiation effects of intravenously administered colloidal Au198 in man. *Cancer* 7, 856-866 (1954).

[15]. Haase, A. et al. Toxicity of silver nanoparticles in human macrophages: uptake, intracellular distribution and cellular responses. *Journal of Physics: Conference Series* 304, 012030 (2011).

[16]. Cheng, Y. et al. Highly Efficient Drug Delivery with Gold Nanoparticle Vectors for in Vivo Photodynamic Therapy of Cancer. *Journal of the American Chemical Society* 130, 10643-10647 (2008).

[17]. Paciotti, G. F., Kingston, D. G. I. & Tamarkin, L. Colloidal gold nanoparticles: a novel nanoparticle platform for developing multifunctional tumor-targeted drug delivery vectors. *Drug Development Research* 67, 47-54 (2006).

[18]. Chan, W. C. W. & Nie, S. Quantum Dot Bioconjugates for Ultrasensitive Nonisotopic Detection. *Science* 281, 2016-2018 (1998).

[19]. Jaiswal, J. K., Mattoussi, H., Mauro, J. M. & Simon, S. M. Long-term multiple color imaging of live cells using quantum dot bioconjugates. *Nat Biotech* 21, 47-51 (2003).

[20]. McCarthy, J. R., Kelly, K. A., Sun, E. Y. & Weissleder, R. Targeted delivery of multifunctional magnetic nanoparticles. *Nanomedicine* 2, 153-167 (2007).

[21]. Maiti, K. K. et al. Development of biocompatible SERS nanotag with increased stability by chemisorption of reporter molecule for in vivo cancer detection. *Biosens Bioelectron* 26, 398-403 (2010).

[22]. Lee, M. et al. Highly reproducible immunoassay of cancer markers on a gold-patterned microarray chip using surface-enhanced Raman scattering imaging. *Biosensors and Bioelectronics* 26, 2135-2141 (2011).

[23]. Kopwitthaya, A. et al. Functionalized Plasmonic Anisotropic Nanocrystals for Multimodal Imaging of Cancer Cells. *Plasmonics* 8, 313-318 (2013).

[24]. Huang, X., Jain, P. K., El-Sayed, I. H. & El-Sayed, M. A. Gold nanoparticles:
interesting optical properties and recent applications in cancer diagnostics and therapy. *Nanomedicine (Lond)* 2, 681-693 (2007).

[25]. Link, S. & El-Sayed, M. A. Spectral Properties and Relaxation Dynamics of Surface Plasmon Electronic Oscillations in Gold and Silver Nanodots and Nanorods. *The Journal of Physical Chemistry B* 103, 8410-8426 (1999).

[26]. Nikoobakht, B. & El-Sayed, M. A. Preparation and Growth Mechanism of Gold Nanorods (NRs) Using Seed-Mediated Growth Method. *Chemistry of Materials* 15, 1957-1962 (2003).

[27]. Orendorff, C. J. & Murphy, C. J. Quantitation of Metal Content in the Silver-Assisted Growth of Gold Nanorods. *The Journal of Physical Chemistry B* 110, 3990-3994 (2006).

[28]. Nikoobakht, B., Wang, J. & El-Sayed, M. A. Surface-enhanced Raman scattering of molecules adsorbed on gold nanorods: off-surface plasmon resonance condition. *Chemical Physics Letters* 366, 17-23 (2002).

[29]. Mohamed, M. B., Ismail, K. Z., Link, S. & El-Sayed, M. A. Thermal Reshaping of Gold Nanorods in Micelles. *The Journal of Physical Chemistry B* 102, 9370-9374 (1998).

[30]. Liu & Guyot-Sionnest, P. Synthesis and Optical Characterization of Au/Ag Core/Shell Nanorods. *The Journal of Physical Chemistry B* 108, 5882-5888 (2004).

[31]. Hodak, J. H., Martini, I. & Hartland, G. V. Spectroscopy and Dynamics of Nanometer-Sized Noble Metal Particles. *The Journal of Physical Chemistry B* 102, 6958-6967 (1998).

[32]. Went, P. T. H. et al. Frequent EpCam protein expression in human carcinomas. *Human Pathology* 35, 122-128 (2004).

[33]. Baeuerle, P. A. & Gires, O. EpCAM (CD326) finding its role in cancer. *Br J Cancer* 96, 417-423 (2007).

[34]. Armstrong, A. & Eck, S. L. EpCAM: A New Therapeutic Target for an Old Cancer Antigen. *Cancer Biology & Therapy* 2, 320-325 (2003).

[35]. Chang, L. & Goldman, R. D. Intermediate filaments mediate cytoskeletal crosstalk. *Nat Rev Mol Cell Biol* 5, 601-613 (2004).

[36]. Adams, T. E., Epa, V. C., Garrett, T. P. J. & Ward*, C. W. Structure and function of the type 1 insulin-like growth factor receptor. *CMLS, Cell. Mol. Life Sci.* 57, 1050-1093 (2000).

[37]. Scheidegger, K. J., Cenni, B., Picard, D. & Delafontaine, P. Estradiol Decreases IGF-1 and IGF-1 Receptor Expression in Rat Aortic Smooth Muscle Cells: MECHANISMS FOR ITS ATHEROPROTECTIVE EFFECTS. *Journal of Biological Chemistry* 275, 38921-38928 (2000).

[38]. Zong, S. et al. A SERS and fluorescence dual mode cancer cell targeting probe based on silica coated Au@Ag core-shell nanorods. *Talanta* 97, 368-375 (2012).

[39]. Qian, X. et al. In vivo tumor targeting and spectroscopic detection with surface-enhanced Raman nanoparticle tags. *Nat Biotech* 26, 83-90 (2008).

[40]. Jiang, J. D., Burstein, E. & Kobayashi, H. Resonant Raman scattering by crystal-violet molecules adsorbed on a smooth gold surface: Evidence for a charge-transfer excitation. *Phys Rev Lett* 57, 1793-1796 (1986).

[41]. Chung, Y.-K. et al. An electrical biosensor for the detection of circulating tumor cells. *Biosensors and Bioelectronics* 26, 2520-2526 (2011).

[42]. Paterlini-Brechot, P. & Benali, N. L. Circulating tumor cells (CTC) detection: Clinical impact and future directions. *Cancer Letters* 253, 180-204 (2007).

[43]. Husemann, Y. et al. Systemic Spread Is an Early Step in Breast Cancer. *Cancer cell* 13, 58-68 (2008).

[44]. Becker, J. et al. Plasmonic focusing reduces ensemble linewidth of silver-coated gold nanorods. *Nano Lett* 8, 1719-1723 (2008).

[45]. Michota, A. & Bukowska, J. Surface-enhanced Raman scattering (SERS) of 4-mercaptobenzoic acid on silver and gold substrates. *Journal of Raman Spectroscopy* 34, 21-25 (2003).

[46]. Kulin, S., Kishore, R., Hubbard, J. B. & Helmerson, K. Real-Time Measurement of Spontaneous Antigen-Antibody Dissociation. *Biophysical journal* 83, 1965-1973 (2002).

What is claimed is:

1. A method of making at least one nanocomposite for surface enhanced Raman spectroscopy (SERS) detection of a target of interest, comprising:
   forming at least one gold nanorod;
   coating a silver layer on an outer surface of the gold nanorod;
   assembling a Raman reporter molecule layer on the coated silver layer, wherein the Raman reporter molecule layer comprises Raman reporter molecules that are detectable by the SERS;
   coating a thiolated polyethylene glycol (PEG) layer on the assembled Raman reporter molecule layer; and
   conjugating the coated thiolated PEG layer with molecules of an antibody to make the at least one nanocomposite,
   wherein said forming the at least one gold nanorod comprises:
   mixing a first hexadecyltrimethylammoniumbromide (CTAB) solution with a silver nitrate solution to form a first mixture;
   adding a first $HAuCl_4$ to the first mixture to form a second mixture;
   adding a first ascorbic acid to the second mixture to form a third mixture;
   adding a seed solution to the third mixture to form a fourth mixture; and centrifuging the fourth mixture to form a first precipitate, wherein the first precipitate comprises the gold nanorod; and wherein the seed solution is prepared by: mixing a second CTAB solution with a second HAuCl₄ to form a fifth mixture; and adding NaBH₄ to the fifth mixture and stirring to form the seed solution;

wherein said coating the silver layer comprises:

dispersing the gold nanorod in a third CTAB solution by sonication to form a sixth mixture;

adding a polyvinylpyrrolidone (PVP) solution and AgNO₃ to the sixth mixture and gently mixing to form a seventh mixture;

adding a second ascorbic acid to the seventh mixture to form an eighth mixture;

adding NaOH solution to the eighth mixture to form a ninth mixture, such that the pH of the ninth mixture is elevated to about pH 9, and a silver ion reduction reaction is initiated; and centrifuging the ninth mixture to form a second precipitate, wherein the second precipitate comprises the gold nanorod coated with the silver layer.

2. The method of claim 1, wherein the step of assembling the Raman reporter molecule layer comprises:

dispersing the gold nanorod coated with the silver layer in distilled water to form a tenth mixture;

dissolving the Raman reporter molecule comprising 4-mercaptobenzoic acid (4-MBA), p-aminothiophenol (PATP), p-nitrothiophenol (PNTP), or 4-(methylsulfanyl) thiophenol (4-MSTP), in ethanol to form a reporter solution;

adding the reporter solution to the tenth mixture and stirring to form an eleventh mixture; and centrifuging the eleventh mixture to form a third precipitate, wherein the third precipitate comprises the gold nanorod coated with the silver layer, and assembled with the Raman report molecule layer.

3. The method of claim 2, wherein the step of coating the thiolated PEG layer comprises:

dispersing the gold nanorod with the coated silver layer and the assembled Raman reporter layer in thiolated polyethylene glycol acid (HS-PEG-COOH) solution and vigorously stirring to form a twelfth mixture, wherein the HS-PEG-COOH solution comprises about 2 mg/ml HS-PEG and about 2 mM NaCl;

adding thiolated polyethylene glycol (HS-PEG) to the twelfth mixture and keep at about 5° C. overnight to form a thirteenth mixture; and centrifuging the thirteenth mixture to form a fourth precipitate, wherein the fourth precipitate comprises the gold nanorod coated with the silver layer, assembled with the Raman report molecule layer, and coated with the thiolated PEG layer.

4. The method of claim 3, wherein the step of conjugating the coated thiolated PEG layer with the molecules of the antibody comprises:

suspending the gold nanorod with the coated silver layer, the assembled Raman reporter layer, and the coated thiolated PEG layer in PBS buffer by sonicating to form a suspending mixture;

adding N-hydroxysuccinimide (NHS) and 1N-ethyl-N'-(3-dimethylaminopropyl) carbodiimide hydrochloride (EDC) to the suspending mixture and stirring to form a fourteenth mixture;

washing the fourteenth mixture by centrifuging twice using PBS buffer to obtain a fifth precipitate;

dispending the fifth precipitate in PBS buffer to form a fifteenth mixture;

adding molecules of the antibody to the fifteenth mixture and mixing thoroughly to form a sixteenth mixture, wherein the antibody comprises anti-EpCAM, anti-CD44, anti-IGF-1 Receptor β, anti-Keratin 18, or one or more antibodies specific to the target of interest; and stirring the sixteenth mixture at room temperature to form the at least one nanocomposite.

5. The method of claim 1, wherein SERS signal corresponding to the at least one nanocomposite is characterized with a predetermined color.

6. The method of claim 1, wherein the target of interest comprises at least one tumor cell or at least one pathogen.

7. The method of claim 1, further comprising attaching at least one molecule of interest to the at least one nanocomposite, wherein the at least one molecule of interest is a drug, a growth factor, a protein, or other biologically active molecules.

8. The method of claim 7, further comprising attaching at least one fluorescent agent to the at least one nanocomposite.

9. A method of making at least one nanocomposite for surface enhanced Raman spectroscopy (SERS) detection of a target of interest, comprising:

forming at least one gold nanorod, comprising:

mixing a first hexadecyltrimethylammoniumbromide (CTAB) solution with a silver nitrate solution to form a first mixture;

adding a first HAuCl₄ to the first mixture to form a second mixture;

adding a first ascorbic acid to the second mixture to form a third mixture;

adding a seed solution to the third mixture to form a fourth mixture; and centrifuging the fourth mixture to form a first precipitate, wherein the first precipitate comprises the gold nanorod;

wherein the seed solution is prepared by:

mixing a second CTAB solution with a second HAuCl₄ to form a fifth mixture; and adding NaBH₄ to the fifth mixture and stirring to form the seed solution;

coating a silver layer on an outer surface of the gold nanorod;

assembling a Raman reporter molecule layer on the coated silver layer, wherein the Raman reporter molecule layer comprises Raman reporter molecules that are detectable by the SERS, wherein the Raman reporter molecule layer comprises p-aminothiophenol (PATP), p-nitrothiophenol (PNTP) or 4-(methylsulfanyl) thiophenol (4MSTP);

coating a thiolated polyethylene glycol (PEG) layer on the assembled Raman reporter molecule layer; and conjugating the coated thiolated PEG layer with molecules of an antibody to make the at least one nanocomposite, wherein said coating the silver layer comprises:

dispersing the gold nanorod in a third hexadecyltrimethylammoniumbromide (CTAB) solution by sonication to form a sixth mixture;

adding a polyvinylpyrrolidone (PVP) solution and AgNO₃ to the sixth mixture and gently mixing to form a seventh mixture;

adding a second ascorbic acid to the seventh mixture to form an eighth mixture;

adding NaOH solution to the eighth mixture to form a ninth mixture, such that the pH of the ninth mixture is elevated to about pH 9, and a silver ion reduction reaction is initiated; and centrifuging the ninth mixture to form a second precipitate, wherein the second precipitate comprises the gold nanorod coated with the silver layer.

\* \* \* \* \*